US 9,433,712 B2

(12) United States Patent
Locke et al.

(10) Patent No.: US 9,433,712 B2
(45) Date of Patent: Sep. 6, 2016

(54) INLINE STORAGE POUCHES FOR USE WITH BODY FLUIDS

(75) Inventors: Christopher Brian Locke, Bournemouth (GB); Elliott Rider, Acklam (GB); Benjamin A. Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 1186 days.

(21) Appl. No.: 13/442,519

(22) Filed: Apr. 9, 2012

(65) Prior Publication Data

US 2013/0053797 A1   Feb. 28, 2013

Related U.S. Application Data

(60) Provisional application No. 61/543,558, filed on Oct. 5, 2011, provisional application No. 61/529,709, filed on Aug. 31, 2011.

(51) Int. Cl.
*A61M 1/00* (2006.01)
*A61M 5/178* (2006.01)
(Continued)

(52) U.S. Cl.
CPC ... *A61M 1/0088* (2013.01); *A61F 2013/00536* (2013.01); *A61M 2205/3344* (2013.01); *A61M 2205/50* (2013.01); *Y10T 29/49826* (2015.01)

(58) Field of Classification Search
CPC ........ A61M 1/00; A61M 5/178; A61M 5/00; A61M 5/32; A61M 35/00; A61F 13/00
See application file for complete search history.

(56) References Cited

U.S. PATENT DOCUMENTS 1,355,846 A   10/1920   Rannells
2,547,758 A   4/1951   Keeling
(Continued)

FOREIGN PATENT DOCUMENTS

AU   550575 A1   8/1982
AU   745271      4/1999
(Continued)

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Tatyana Zalukaeva
*Assistant Examiner* — Ilya Treyger

(57) ABSTRACT

Inline storage pouches and systems for receiving and retaining body fluids from an animal are presented. The inline storage pouch include a flexible pouch body has an interior portion with a fluid storage material disposed within the interior portion. In addition to receiving body fluids, the inline storage pouch may fluidly couple a pressure sensing conduit between a first port and a second port using a first bypass conduit. The first port may be a patient-port interface. The second port may be a device-port interface. Multiple sensors and bypass conduits may be included and associated with a microprocessor that is configured to locate blockages or determine when the inline storage pouch is full. Another inline storage pouch has two chambers and receives and discharges fluids from a pouch connector. Other pouches, systems, and methods are presented herein.

26 Claims, 17 Drawing Sheets

(51) Int. Cl.
   *A61M 5/00*      (2006.01)
   *A61M 5/32*      (2006.01)
   *A61M 35/00*     (2006.01)
   *A61F 13/00*     (2006.01)

(56)          References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,973,562 A | 8/1976 | Jansson |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,792,126 A * | 8/1998 | Tribastone .......... A61M 1/0001 604/319 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,034,038 B2 * | 10/2011 | Biggie ................ A61M 1/0088 602/42 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0084838 A1 | 4/2005 | Lampeter |
| 2007/0032762 A1 | 2/2007 | Vogel |
| 2008/0011368 A1 | 1/2008 | Singh |
| 2011/0172616 A1* | 7/2011 | Hartwell ............ A61M 1/0001 604/319 |
| 2011/0196321 A1* | 8/2011 | Wudyka ............. A61M 1/0001 604/319 |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | WO94/28996 A1 | 12/1994 |

(56) References Cited

FOREIGN PATENT DOCUMENTS

| WO | 96/05873 | 2/1996 |
|---|---|---|
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding PCT/US2012/032804, mailed Aug. 7, 2012.
Written Opinion and International Search Report based on corresponding PCT Application No. PCT/US2012/032804 mailed Aug. 7, 2012.

* cited by examiner

INLINE STORAGE POUCHES FOR USE WITH BODY FLUIDS

RELATED APPLICATIONS

The present invention claims the benefit, under 35 USC §119(e), of the filings of U.S. Provisional Patent Application Ser. No. 61/543,558, entitled "INLINE STORAGE POUCHES FOR USE WITH BODY FLUIDS," filed on 5 Oct. 2011, which is incorporated herein by reference for all purposes; and U.S. Provisional Patent Application Ser. No. 61/529,709, entitled "EVAPORATIVE FLUID POUCH AND SYSTEMS FOR USE WITH BODY FLUIDS," filed 31 Aug. 2011, which is incorporated herein by reference for all purposes.

TECHNICAL FIELD

The present disclosure relates generally to medical treatment systems for treating tissue sites that produce liquids, such as exudate, and for processing body fluids. More particularly, but not by way of limitation, the present disclosure relates to inline storage pouches, systems, and methods for receiving and storing liquids from an animal.

BACKGROUND

Caring for wounds is important in the healing process. Wounds often produce considerable liquids, e.g., exudate. Medical dressings are often used in wound care to address the production of liquids from the wound. If not properly addressed, liquids at the wound can lead to infection or maceration at or near the wound. As used throughout this document, "or" does not require mutual exclusivity. Wound dressings may be used alone or as an aspect of applying reduced pressure to a tissue site.

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, an inline storage pouch for use with body fluids from an animal includes a flexible pouch body having an interior portion, a fluid storage material disposed within the interior portion, and a first port. As used herein, it should be understood that the term "animal" includes humans. The first port is formed on the flexible pouch body and is configured to connect to a first multi-lumen conduit extending from the flexible pouch body to the animal. The first multi-lumen conduit has at least one sensing lumen and at least one reduced pressure lumen. The inline storage pouch also includes a second port formed on the flexible pouch body. The second port is configured to fluidly connect to a second multi-lumen conduit extending from the flexible pouch body to a reduced pressure source. The second multi-lumen conduit has at least one sensing lumen and at least one reduced pressure lumen.

The inline storage pouch also includes a first bypass conduit disposed within and fluidly isolated from the interior portion of the flexible pouch body. The first bypass conduit has a first end and a second end. The first end of the first bypass conduit is fluidly coupled to the at least one sensing lumen of the first multi-lumen conduit. The second end of the first bypass conduit is fluidly coupled to the at least one sensing lumen of the second multi-lumen conduit. The first port may be a patient-port interface. The second port may be a device-port interface.

According to another illustrative embodiment, a system for treating a tissue site on an animal with reduced pressure includes a wound dressing for disposing proximate to the tissue site for providing reduced pressure to the tissue site. The wound dressing has a reduced-pressure interface. The reduced-pressure interface includes a reduced-pressure-supply conduit and a pressure-assessment conduit. The system further includes an inline storage pouch, a first multi-lumen conduit, and a second multi-lumen conduit. The first multi-lumen conduit has at least one sensing lumen and at least one reduced pressure lumen. The at least one sensing lumen of the first multi-lumen conduit is fluidly coupled to the pressure-assessment conduit of the reduced-pressure interface. The at least one reduced-pressure lumen of the first multi-lumen conduit is fluidly coupled to the reduced-pressure-supply conduit.

The inline storage pouch includes a flexible pouch body having an interior portion, a fluid storage material disposed within the interior portion, a first port formed on the flexible pouch body configured to connect to the first multi-lumen conduit, and a second port formed on the flexible pouch body. The second port is configured to fluidly couple to a second multi-lumen conduit that extends from the flexible pouch body to a reduced pressure source. The second multi-lumen conduit has at least one sensing lumen and at least one reduced pressure lumen. The inline storage pouch also includes a first bypass conduit disposed within and fluidly isolated from the interior portion of the flexible pouch body. The bypass conduit has a first end and a second end. The first end of the bypass conduit is fluidly coupled to the at least one sensing lumen of the first multi-lumen conduit. The second end of the bypass conduit is fluidly coupled to the at least one sensing lumen of the second multi-lumen conduit.

The system also includes a reduced-pressure source and a first pressure-sensing unit. The at least one reduced pressure lumen of the second multi-lumen conduit is fluidly coupled to the reduced-pressure source. The at least one sensing lumen of the second multi-lumen conduit is fluidly coupled to the first-pressure sensing device.

According to another illustrative embodiment, a method of storing liquids from an animal includes providing an inline storage pouch. The inline storage pouch includes a flexible pouch body having an interior portion, a fluid storage material disposed within the interior portion, and a first port. The first port is formed on the flexible pouch body. The first port is configured to connect to a first multi-lumen conduit that extends from the flexible pouch body to the animal. The first multi-lumen conduit has at least one sensing lumen and at least one reduced pressure lumen.

The inline storage pouch also includes a second port formed on the flexible pouch body. The second port is configured to fluidly connect to a second multi-lumen conduit that extends from the flexible pouch body to a reduced pressure source. The second multi-lumen conduit has at least one sensing lumen and at least one reduced pressure lumen. The inline storage pouch also includes a first bypass conduit disposed within and fluidly isolated from the interior portion of the flexible pouch body. The first bypass conduit has a first end and a second end. The first end of the first bypass conduit is fluidly coupled to the at least one sensing lumen of the first multi-lumen conduit. The second end of the first bypass conduit is fluidly coupled to the at least one sensing lumen of the second multi-lumen conduit.

The method also includes coupling the at least one reduced pressure lumen of the first multi-lumen conduit to the animal to receive the liquids from the animal and coupling the at least one sensing lumen of the first multi-lumen conduit to the animal to receive the pressure from the animal proximate to where the liquids are removed. The method also includes providing reduced pressure to the at least one reduced pressure lumen of the second multi-lumen conduit and coupling a pressure-sensing unit to the at least one sensing lumen of the second multi-lumen conduit.

According to another illustrative embodiment, an inline storage pouch for use with body fluids from an animal includes a flexible pouch body having a first wall, a second wall, and a partitioning wall whereby an interior portion is formed. The interior portion has a first chamber and a second chamber. The flexible pouch body has a proximal end and a distal end. The inline storage pouch also includes a first manifolding material disposed within the first chamber and a fluid storage material disposed within the second chamber. The inline storage pouch further includes a pouch connector coupled to the flexible pouch body at the proximal end. The pouch connector fluidly couples fluids received from the animal to the second chamber and fluidly couples reduced pressure received from a reduced-pressure source to the first chamber. The partitioning wall of the flexible pouch body has a proximal end and a distal end, and the proximal end of the partitioning wall has an exudate aperture for receiving a portion of the pouch connector. The distal end of the partitioning wall has a return aperture for allowing fluid flow from the second chamber to the first chamber.

According to another illustrative embodiment, a pouch connector for use with an inline storage pouch includes a connector body formed with an exudate chamber having an intake port for receiving the fluids from the animal and an outlet for discharging the fluids. The connector body is also formed with a reduced-pressure chamber having an intake port for receiving fluids and an outlet port for discharging fluids. The outlet port of the reduced-pressure chamber is for receiving the reduced pressure from the reduced-pressure source. The exudate chamber and reduced-pressure chamber are fluidly isolated from each other within the pouch connector. The pouch connector also includes a displacement conduit fluidly coupled to the outlet port of the exudate chamber for delivering the fluids from the exudate chamber to a portion of the inline storage pouch. The intake port of the reduced-pressure chamber is fluidly coupled to another portion of the inline storage pouch for delivering reduced pressure thereto.

According to another illustrative embodiment, a method of manufacturing an inline storage pouch for use with body fluids from an animal includes forming a flexible pouch body having a first wall, a second wall, and a partitioning wall whereby an interior portion is formed having a first chamber and a second chamber. The flexible pouch body has a proximal end and a distal end. The method further includes disposing a first manifolding material within the first chamber, disposing a fluid storage material within the second chamber, and coupling a pouch connector to the flexible pouch body at the proximal end. The pouch connector fluidly couples fluids from the animal to the second chamber and fluidly couples reduced pressure received from a reduced-pressure source to the first chamber. The partitioning wall of the flexible pouch body has a proximal end and a distal end. The method further includes forming an exudate aperture proximate the proximal end of the partitioning wall, disposing a portion of the pouch connector through the exudate aperture, and forming a return aperture proximate the distal end of the partitioning wall for allowing fluid flow from the second chamber into the first chamber.

Other aspects, features, and advantages of the illustrative embodiments will become apparent with reference to the drawings and detailed description that follow.

DETAILED DESCRIPTION OF ILLUSTRATIVE EMBODIMENTS

Figure 1:
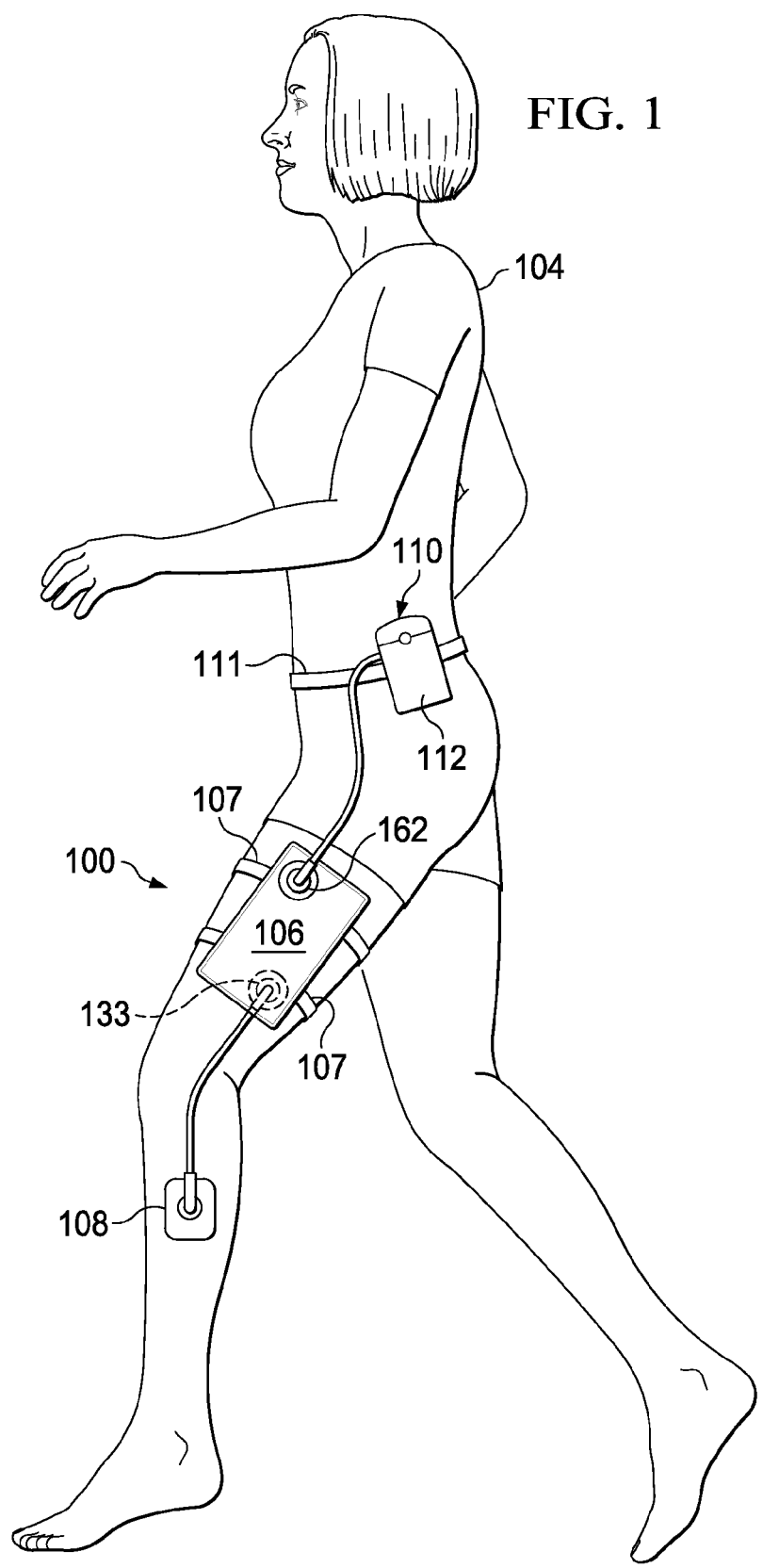
FIG. 1 is a schematic, perspective view of an illustrative system for treating a tissue site on an animal with reduced pressure that involves storing liquids in an inline storage pouch.

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Referring now to the drawings and initially to FIGS. 1-7, an illustrative embodiment of a system 100 for treating a tissue site 102 on an animal 104, which is deemed to include a human as shown, with reduced pressure is presented. The system 100 includes an inline storage pouch 106. The system 100 is shown on a human, but the system 100 may be used on any animal 104, e.g., horse, cow, dog, pig, turtle, etc. The system 100 includes a wound dressing 108 (or other fluid reception device), the inline storage pouch 106, and a therapy unit 110, which includes a reduced-pressure source 112. Liquids are delivered to the inline storage pouch 106 for storing. The liquids are removed from the animal 104 using reduced pressure. The liquids are from a tissue site 102, e.g., a wound site, but could also be from an ostomy bag or another source.

The system 100 may allow the user to position the weight of the inline storage pouch 106 and the therapy unit 110 at different locations on the animal. In other words, the weight of the components of the system 100 may be distributed at different locations as suggested in FIG. 1. Thus, the inline storage pouch 106 may be strapped to a portion of the animal 104, such as a leg, using straps 107 (or other attachment devices). At the same time, the therapy unit 110 may be attached at another location on the animal 104, e.g., a torso, using straps 111.

The inline storage pouch 106 is flexible. The flexibility allows the inline storage pouch 106 to conform to a portion of the animal's body thereby enhancing safety and comfort. In addition, the flexible nature of the inline storage pouch 106 allows the inline storage pouch 106 to be stored in a small space. The inline storage pouch 106 is relatively easy to manufacture compared to rigid canisters that have been used to collect liquids. Moreover, when the inline storage pouch 106 is used with non-human animals, the flexible nature may help prevent injury when the animal bumps surfaces or rolls over.

Figure 2:
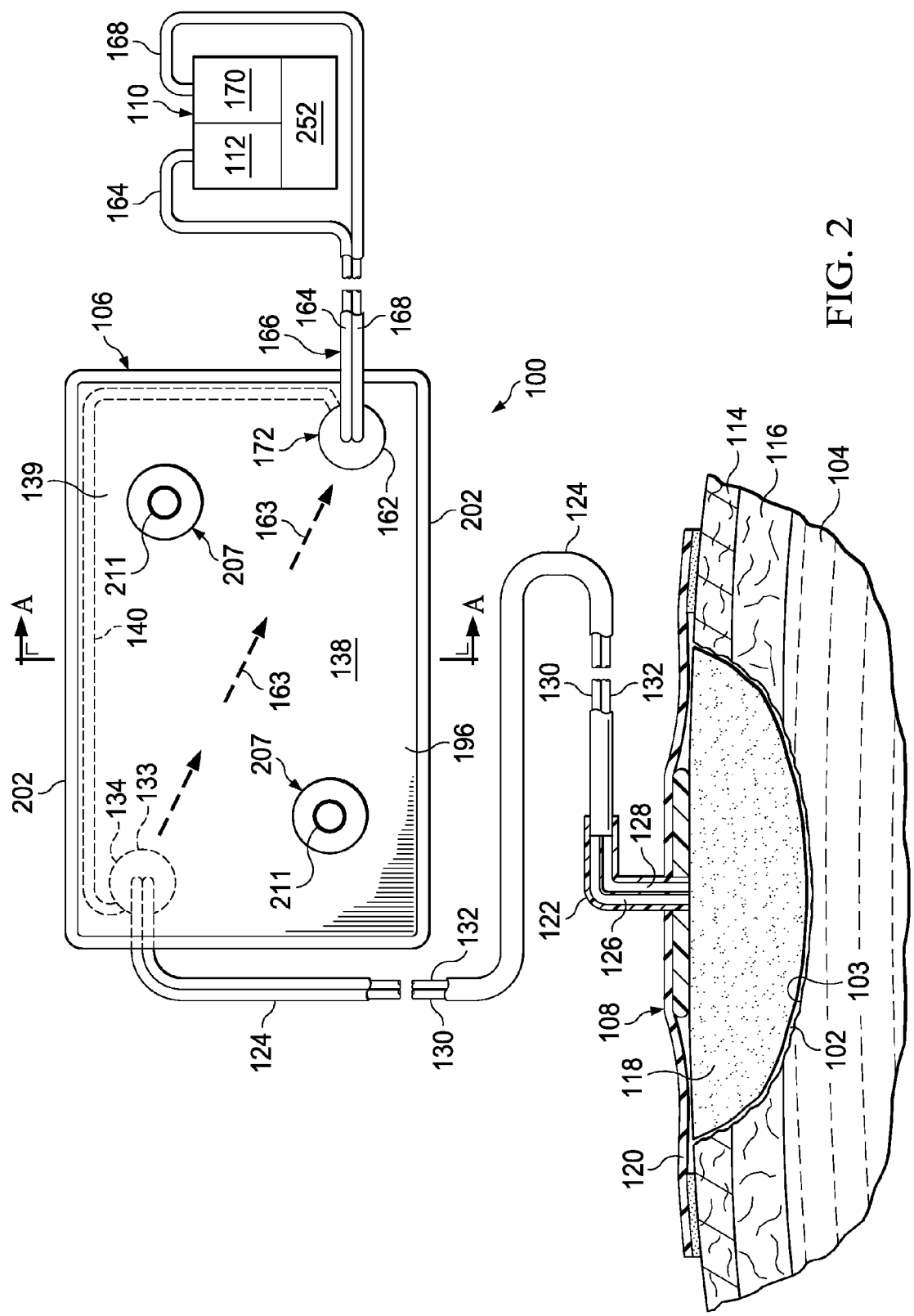
FIG. 2 is a schematic diagram, with a portion shown in cross section and a portion in plan view, of an illustrative system for treating a tissue site on an animal with reduced pressure that involves storing liquids in an inline storage pouch.

As shown best in FIG. 2, a wound 103 at tissue site 102 is through epidermis 114 and into dermis 116. The wound dressing 108 is disposed on the tissue site 102, e.g., the wound 103, and is operable to receive fluids from the tissue site 102. The wound dressing 108 may be any type of dressing for receiving fluids from the patient, but is shown as a dressing with a wound-interface manifold 118 and a drape 120. The wound dressing 108 may be any device that collects liquids whether a wound is involved or not. For example, in one illustrative embodiment, the wound dressing 108 may be a device for removing liquids from an ostomy bag. Typically, however, the wound dressing 108 is for removing liquids from a wound 103. Fluids, including liquids, from the tissue site 102 are delivered through a reduced-pressure interface 122 to a first multi-lumen conduit 124. The first multi-lumen conduit 124 is fluidly coupled to the inline storage pouch 106.

The reduced-pressure interface 122 includes a reduced-pressure-supply conduit 126 and a pressure-assessment conduit 128. The reduced-pressure-supply conduit 126 is fluidly coupled to a reduced-pressure lumen 130 in the first multi-lumen conduit 124. The pressure-assessment conduit 128 is fluidly coupled to a sensing lumen 132 in the first multi-lumen conduit 124. In one illustrative embodiment, the reduced-pressure interface 122 is a T.R.A.C.® Pad or Sensa T.R.A.C.® Pad available from KCI of San Antonio, Tex. The reduced-pressure interface 122 may be any device capable of accomplishing at least two functions: (1) fluidly coupling the reduced-pressure lumen 130 to the wound dressing 108 to deliver reduced pressure to the desired area and (2) fluidly coupling the sensing lumen 132 to a sealed space created by the drape 120.

The first multi-lumen conduit 124 is coupled to the inline storage pouch 106 at a first port 133. The first port 133 is formed on (including coupled to) the flexible pouch body 138. The flexible pouch body 138 has a first side 139 and a second, animal-facing side 141. The first port 133 may be formed on either side 139, 141, but is shown on the second, animal-facing side 141.

The first port 133 may be any device that accomplishes at least a couple functions. First, the first port 133 fluidly couples the reduced-pressure lumen 130 of the first multi-lumen conduit 124 to an interior portion 136 (see FIG. 7) of a flexible pouch body 138. Second, the first port 133 fluidly couples the sensing lumen 132 of the first multi-lumen conduit 124 to a first bypass conduit 140. The first bypass conduit 140 is formed in the interior portion 136 of the flexible pouch body 138 and yet is fluidly isolated from the interior portion 136. For example, without, limitation, the first port 133 may be a patient-port interface 134.

Figure 3:
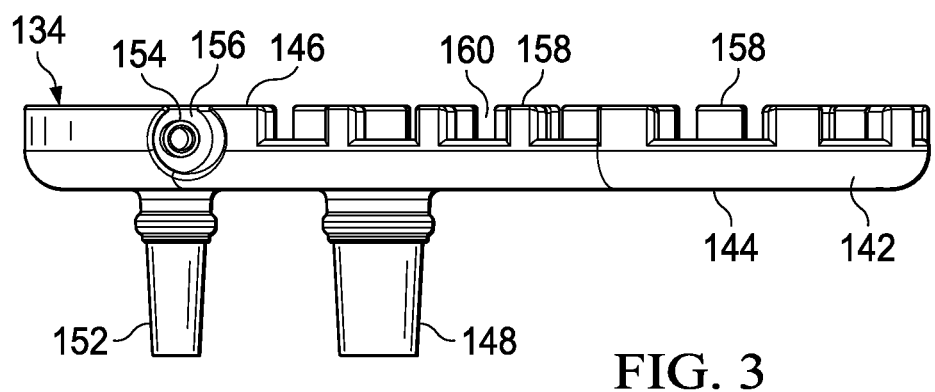
FIG. 3 is a schematic, elevation view of an illustrative patient-port interface.
Figure 4:
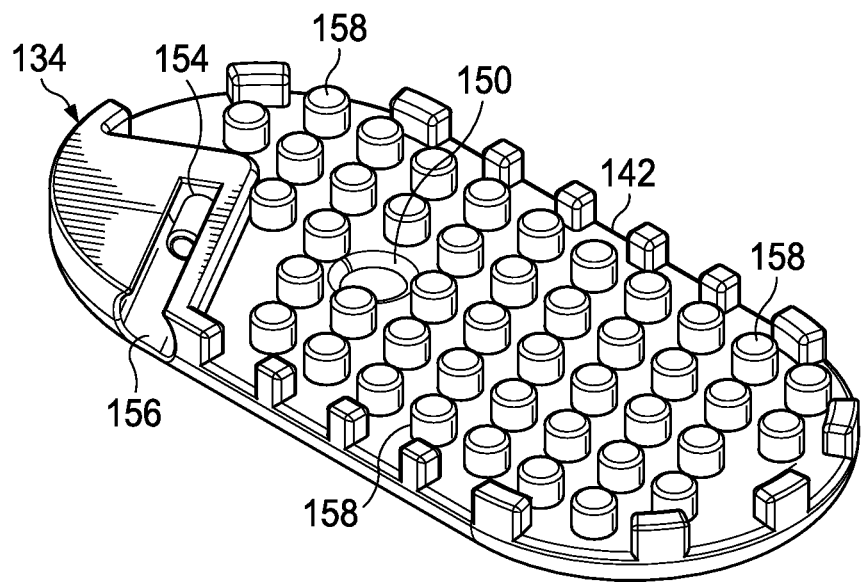
FIG. 4 is a schematic, perspective view showing a pouch-facing side of the patient-port interface of FIG. 3.

Referring now primarily to FIGS. 3-4, an illustrative embodiment of the patient-port interface 134 is presented. The patient-port interface 134 includes a patient-port body 142 having a first side 144 and a second, pouch-facing side 146. The patient-port body 142 also includes a first hollow attachment connector 148 sized and configured for mating with the at least one reduced pressure lumen 130 of the first multi-lumen conduit 124. The first hollow attachment connector 148 is fluidly coupled to a first fluid outlet 150 formed on the patient-port body 142. The patient-port interface 134 may be coupled to either the first 139 or second, animal-facing side 141 of the flexible pouch body 138.

The patient-port body 142 also includes a second hollow attachment connector 152 sized and configured for mating with the at least one sensing lumen 132 of the first multi-lumen conduit 124. The second hollow attachment connector 152 is fluidly coupled to a first pressure-sensing connector 154 on the second, pouch-facing side 146. The first pressure-sensing connector 154 is fluidly coupled to a first end of the first bypass conduit 140. The first pressure-sensing connector 154 may be substantially parallel to the surface of the second, pouch-facing side 146 and may include a conduit-channel 156. A first plurality of offsets 158 is formed on the second, pouch-facing side 146 of the patient-port body 142 for providing flow space 160. The flow space 160 assures space for reduced pressure to move fluids. In other words, the flow space 160 provides space for the fluids to expand and manifold into a fluid storage material 204 or other portion of the interior portion 136.

Referring now primarily to FIGS. 1-4, fluids are moved via pressure differential from the first fluid outlet 150 across the interior portion 136 of the inline storage pouch 106 to a second port 162 as suggested by arrows 163. The fluid is distributed throughout the interior portion 136 as the reduced pressure draws from the second port 162. The second port 162 fluidly couples the interior portion 136 to a second reduced-pressure lumen 164 of a second multi-lumen conduit 166. The second port 162 is shown coupled to the first side 139 of the flexible pouch body 138. The second port 162 may also be formed on the second, animal-facing side 141. Typically, the first port 133 and second port 162 are on opposite sides 139, 141 of the flexible pouch body 138.

The second reduced-pressure lumen 164 is fluidly coupled to the reduced-pressure source 112 of the therapy unit 110. The first bypass conduit 140 delivers fluid from the first port 133 to the second port 162. The first bypass conduit 140 is fluidly isolated from fluids in the interior portion 136 of the flexible pouch body 138. The second port 162 fluidly couples the first bypass conduit 140 to a second sensing lumen 168 of the second multi-lumen conduit 166. The second sensing lumen 168 may be fluidly coupled to a pressure sensing unit 170 of the therapy unit 110. The second port 162 may be any device that accomplishes at least two functions. First, the second port 162 fluidly couples the first bypass conduit 140 to the second sensing lumen 168. Second, the second port 162 fluid couples the second reduced-pressure lumen 164 to the interior portion 136 of the flexible pouch body 138. In one illustrative embodiment, the second port 162 is a device-port interface 172.

Figure 5:
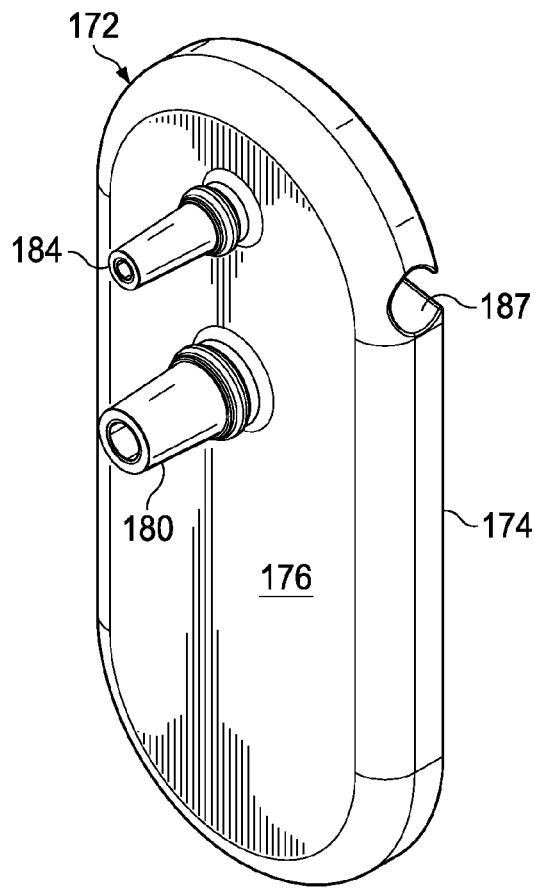
FIG. 5 is a schematic, perspective view showing a first side (opposite the pouch-facing side) of an illustrative embodiment of a device-port interface.
Figure 6:
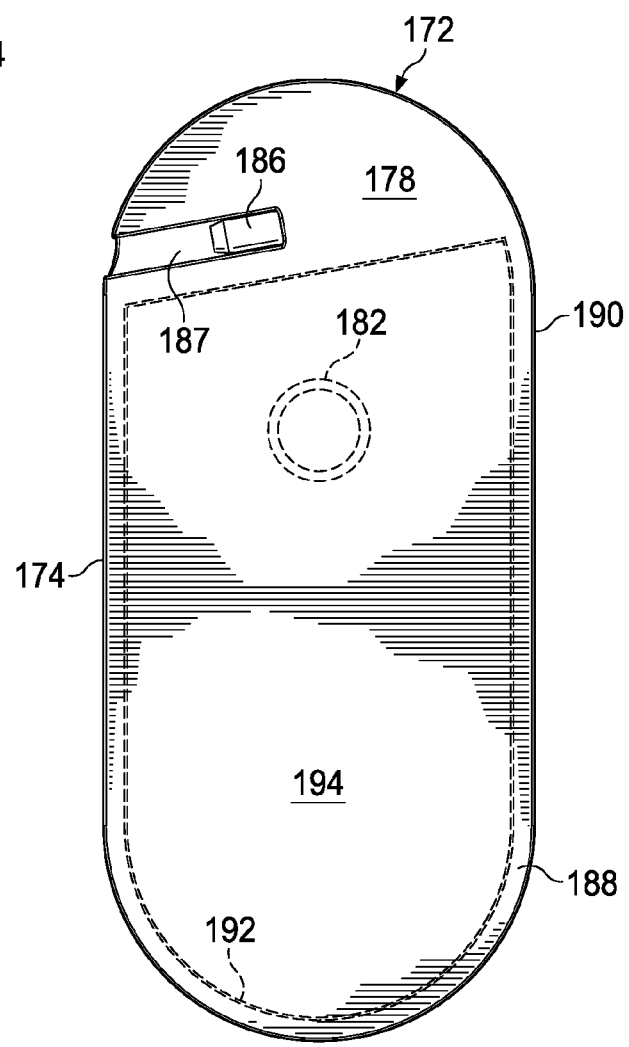
FIG. 6 is a schematic, plan view of a second, pouch-facing side of the illustrative embodiment of the device-port interface of FIG. 5.

Referring now primarily to FIGS. 5-6, an illustrative embodiment of a device-port interface 172 is presented. The device-port interface 172 includes a device-port body 174 having a first side 176 and a second, pouch-facing side 178. The device-port body 174 includes a third hollow attachment connector 180 sized and configured for mating with the second reduced-pressure lumen 164. The third hollow attachment connector 180 is fluidly coupled to a fluid inlet 182. The third hollow attachment connector 180 is formed on (including coupled to) the device-port body 174.

The device-port body 174 also includes a fourth hollow attachment connector 184 sized and configured for mating with the second sensing lumen 168 of the second multi-lumen conduit 166. A second pressure-sensing connector 186 is fluidly coupled to the fourth hollow attachment connector 184. The second pressure-sensing connector 186 is fluidly coupled to a second end of the first bypass conduit 140. The second pressure-sensing connector 186 may be substantially parallel to the surface of the second, pouch-facing side 178 and may include a conduit-channel 187.

The device-port interface 172 may further include an offset 188 formed on the second, pouch-facing side 178 of the device-port body 174 for providing a filter space 192 for one or more hydrophobic filters with bacterial filtering properties. In this embodiment, the offset 188 is a wall 190 that forms the filter space 192. A filter 194 or multiple filters are disposed within the filter space 192. The filter 194 may be any material that prevents liquids from entering the fluid inlet 182. In one embodiment, the filter 194 includes a hydrophobic filter member, a manifolding material, and another hydrophobic filter member or any permutation thereof or functional device to prevent liquids from entering the fluid inlet 182. The filter 194 or filters are hydrophobic, bacterial filtering membranes that are located to prevent fluids and bacteria from progressing towards the therapy unit 110. As an illustrative, non-limiting embodiment, the filter membrane may be a GORE® MMT314 material available from W. L. Gore & Associates, Inc., Newark, Del. The one or more filters 194 are displaced from the base of the device-port interface 172 by castilated surface features (not explicitly shown) or other surface features designed to provide an open area of filter for flow. A charcoal filter may also be included to remove odor. In another illustrative embodiment, a porous polymer, gel-blocking filter may be included in the second reduced-pressure lumen 164.

Figure 7:
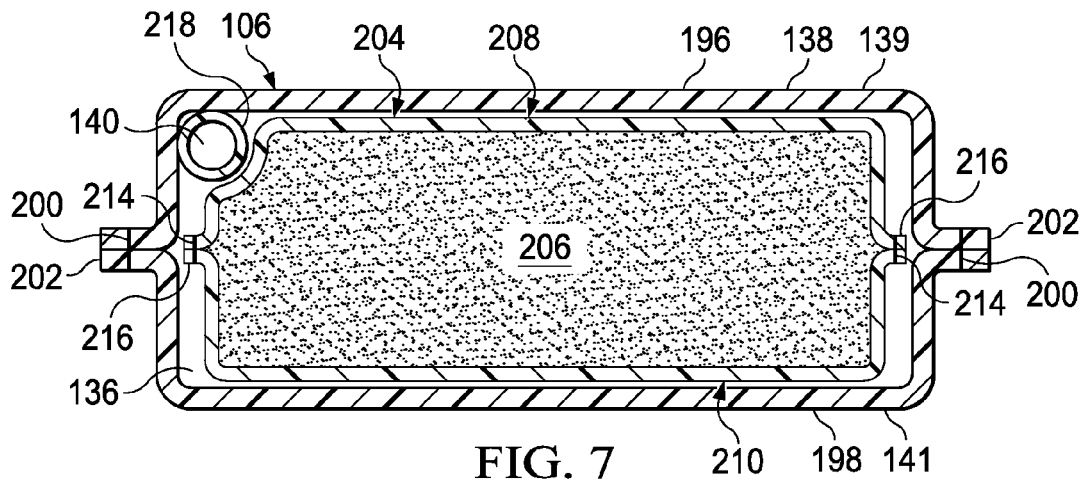
FIG. 7 is a schematic cross section of an illustrative embodiment of the inline storage pouch shown in FIG. 2 taken along line A-A.

Referring now primarily to FIGS. 1-2 and 7, the flexible pouch body 138 of the inline storage pouch 106 is formed with a first wall 196 and a second wall 198. The two walls 196, 198 are coupled or formed as a single unit to form the flexible pouch body 138. The flexible pouch body 138 has the interior portion 136 formed between the walls 196, 198. For example, in one illustrative embodiment, the first wall 196 and the second wall 198 are coupled by an attachment 200 at a peripheral edge 202 of the walls 196, 198. The attachment 200 may be formed using any known technique, including without limitation welding (e.g., ultrasonic or RF welding), bonding, adhesives, cements, stitching, staples, or another coupling device.

The first wall 196 and second wall 198 may be formed from any flexible, liquid-impermeable material. For example, the first wall 196 and second wall 198 may be formed from one or more of the following: natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, silicones, silicone drape, a 3M Tegaderm® drape, or a polyurethane (PU) drape such as one available from Avery Dennison Corporation of Pasadena, Calif., or other appropriate material. The inline storage pouch 106 may be sized to accommodate the quantity of liquid anticipated for a typical treatment time. In one illustrative, non-limiting embodiment, the interior portion 136 has a volume greater than 180 milliliters and less than 500 milliliters, but numerous sizes may be used.

The interior portion 136 formed by the flexible pouch body 138 may be filled at least in part by the fluid storage material 204. The storage material 204 may be formed from any material that receives fluids, including liquids; retains the fluids; and allows reduced pressure to be transmitted. In the illustrative embodiment of FIG. 7, the fluid storage material 204 comprises an absorbent member 206, a first wicking member 208, and a second wicking material 210. The absorbent member 206 may be any material that retains liquids and may comprise one or more of the following: Luquafleece® material, BASF 402c, Technical Absorbents 2317 available from Technical Absorbents (www.techabsorbents.com), sodium polyacrylate super absorbers, cellulosics (carboxy methyl cellulose and salts such as sodium CMC), or alginates. The first wicking member 208 and second wicking member 210 may be formed from one or more of the following: non-woven fabrics such as Libeltex TDL2 or other non-wovens from LIBELTEX bvba of Belgium (www.libeltex.com), woven fabrics including 3D spacer fabrics and Textiles (Baltex, Ilkeston, Derby, UK), open-cell foam, or sintered polymers. The wicking members 208, 210 may be formed by multiple layers of wicking materials that have been stacked or layered.

The first wicking member 208 and the second wicking member 210 may be disposed adjacent to one another at least at their peripheral edges 216 and coupled with an attachment 214 (analogous to attachment 200 as previously described). Thus, the wicking members 208, 210 surround the absorbent member 206. The peripheral edges 216 form overlapping portions and are held in contact with one another to provide a fluid coupling between the wicking members 208, 210. The wicking members 208, 210 may thus be in fluid communication with each other. The wicking members 208, 210 allow fluid flow between the wicking members 208, 210 and along the wicking members 208, 210 at times when the flow of fluid in the absorbent member 206 is inhibited or blocked. In this embodiment, the first bypass conduit 140 comprises a tube 218, but it could also be a web member 212 attached against a portion of wall 196 (FIG. 11), or any device that provides a path to move fluid through the interior portion 136 while remaining fluidly isolated from the interior portion 136.

Figure 8:
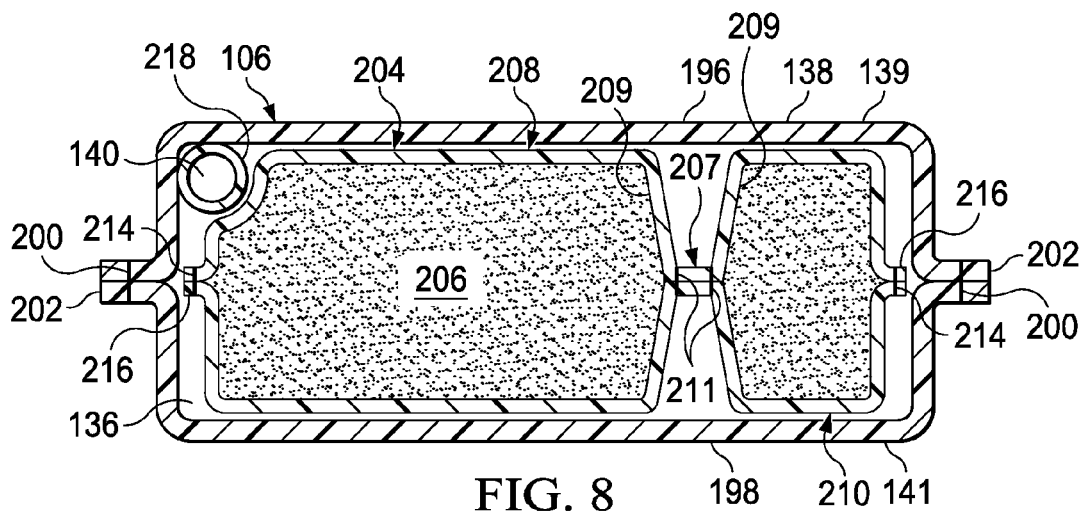
FIG. 8 is a schematic cross section of an illustrative embodiment of the inline storage pouch shown in FIG. 2 taken parallel to line A-A and through an optional fluid-communication button.

Referring now primarily to FIGS. 2 and 8, another illustrative inline storage pouch 106 is presented. The inline storage pouch 106 is analogous in most respects to the inline storage pouch 106 of FIGS. 1, 2, and 7, and accordingly, some parts are labeled but not further described here. In this embodiment, the primary difference is that the flexible pouch body 138 is formed with one or more optional fluid-communication buttons 207.

Each fluid communication-button 207 may be formed by creating an aperture 209 in the absorbent member 206. The first wicking member 208 and second wicking member 210 are brought into contact in the aperture 209, and first wicking member 208 and second wicking member 210 are attached at or near the point of contact. The wicking members 208, 210 are attached using one or more attachments 211 (analogous to 214). This embodiment may be particularly useful in minimizing pressure drop across the inline storage pouch 106 when the wicking members 208, 210 are formed from a non-woven manifolding material. The fluid-communication buttons 207 enhance the degree of fluid communication between the first wicking member 208 and second wicking member 210.

Figure 9:
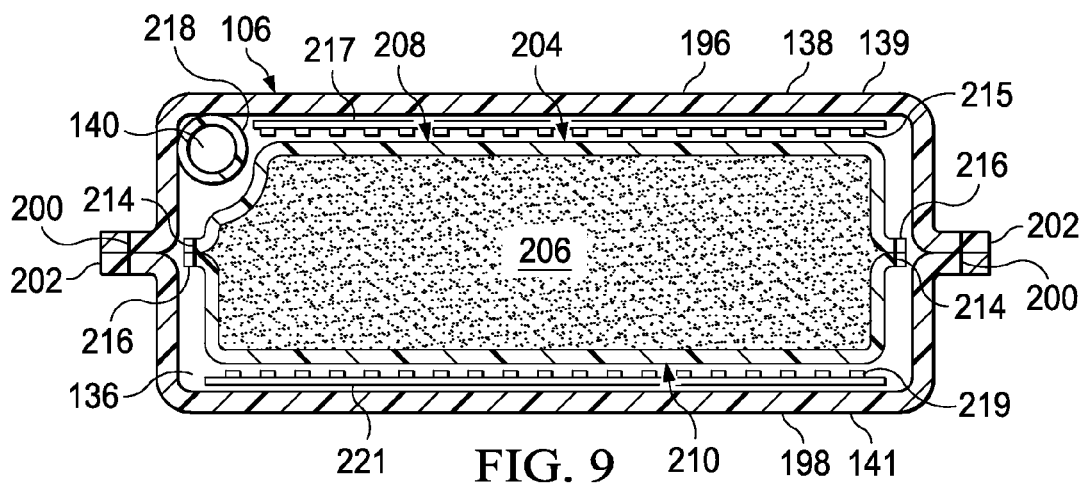
FIG. 9 is a schematic cross section of another illustrative embodiment of the inline storage pouch shown in FIG. 2 taken along line A-A.

Referring now primarily to FIGS. 2 and 9, another illustrative inline storage pouch 106 is presented. The inline storage pouch 106 is analogous in most respects to the inline storage pouch 106 of FIGS. 1, 2, and 7-8, and accordingly, some parts are labeled but not further described here. The primary difference in this embodiment is that a first plurality of offsets 215 has been formed and disposed between the first wall 196 and the fluid storage material 204. In this embodiment, the first plurality of offsets 215 may be positioned between the first wall 196 and the first wicking member 208. The first plurality of offsets 215 may include a first base 217.

The inline storage pouch 106 may also include a second plurality of offsets 219. The second plurality of offsets 219 may be disposed between the second wall 198 and the fluid storage material 204. In this embodiment, the second plurality of offsets 219 may be positioned between the second wicking member 210 and the second wall 198. The second plurality of offsets 219 may include a second base 221. The offsets 215, 219 create additional space for the flow of reduced pressure within the interior portion 136. The inline storage pouch 106 of FIG. 9 may be used with a high-vapor-transfer-rate material as described in connection with FIG. 14 below, but typically the first base 217 and second base 221 would be perforated.

The offsets 215, 219 may formed from any rigid or semi-rigid material approved for use in a body. The offsets 215, 219 are typically formed from a non-absorbent material. The offsets 215, 219 may be formed, for example, from a high-impact polystyrene and may be vacuumed formed to a desired shape (e.g., cylinder, tube, cone, or other shape) and sized as desired for the chamber or interior space. The offsets 215, 219 with their respective bases 217, 221 are flexible and reduced pressure can pass in between the offsets, i.e., through the bases 217, 221, which may permeable or perforated. The offsets 215, 219 facilitate open flow for reduced pressure transmission under compression. The offsets 215, 219 may vary in quantity and pattern or shape and size but should allow pressure to be transmitted and the inline storage pouch 106 to remain flexible. In one illustrative embodiment, the offsets 215, 219 may be any shape or size that provides clearance of at least 1 mm.

Figure 10:
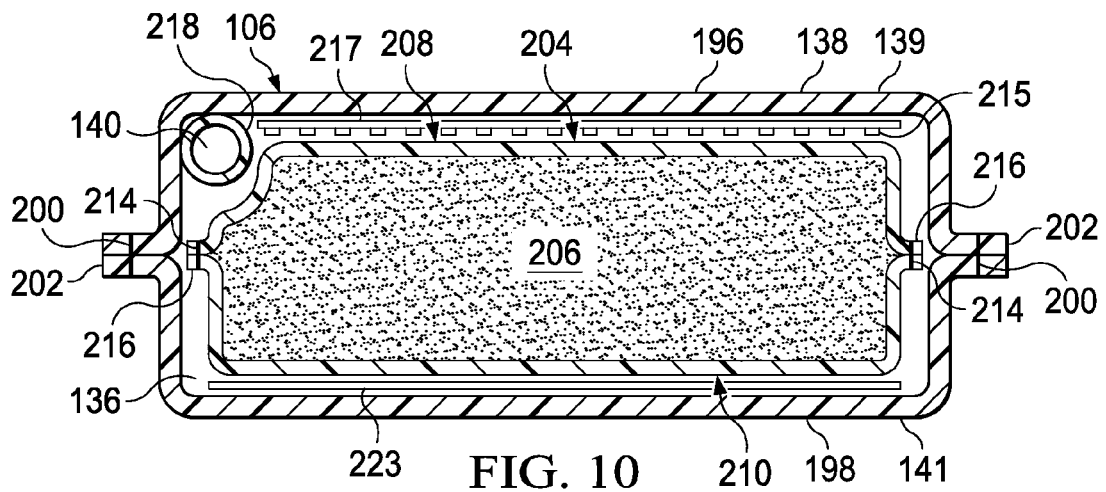
FIG. 10 is a schematic cross section of another illustrative embodiment of the inline storage pouch shown in FIG. 2 taken along line A-A.

Referring now primarily to FIG. 10, another illustrative inline storage pouch 106 is presented. The inline storage pouch 106 is analogous in most respects to the inline storage pouch 106 of FIGS. 1, 2, and 7-9, and accordingly, some parts are labeled but not further described here. The primary difference in this embodiment is that the inline storage pouch 106 includes a first plurality of offsets 215 and a third wicking member 223. As in FIG. 9, the first plurality of offsets 215 are disposed between the first wall 196 and the fluid storage material 204 to create additional flow space for reduced pressure to flow. The third wicking member 223 may be disposed between the second wall 198 and the fluid storage material 204. The third wicking member 223 may be formed from the same materials as the first wicking member 208.

In this embodiment, the third wicking member 223 may be disposed between the second wall 198 and the second wicking member 210. The third wicking member 223 provides additional manifolding material for fluid flow. In other embodiments, additional wicking members may be added in addition to the third wicking member 223. Moreover, in other embodiments, one or more additional wicking members may be added between the first wall 196 and the absorbent member 206.

Figure 11:
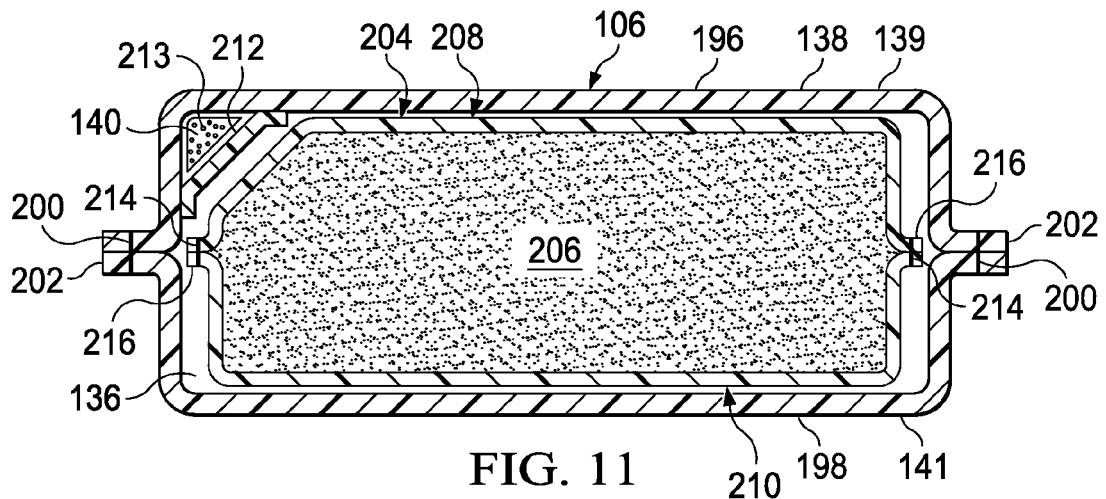
FIG. 11 is a schematic cross section of another illustrative embodiment of the inline storage pouch shown in FIG. 2 taken along line A-A.

Referring now primarily to FIG. 11, another illustrative inline storage pouch 106 is shown in cross section. The inline storage pouch 106 is analogous in most respects to the inline storage pouch 106 of FIGS. 1, 2, and 7-10, and accordingly, some parts are labeled but not further described here. In this illustrative embodiment, a first bypass conduit 140 may be formed by the web member 212 attached against the portion of wall 196. The web member 212 may be formed from the same material as the first wall 196. The first bypass conduit 140 includes a conduit-manifold material 213. The conduit-manifold material 213 may be any material that is sufficient to prevent the first bypass conduit 140 from collapsing under reduced pressure.

Figure 12:
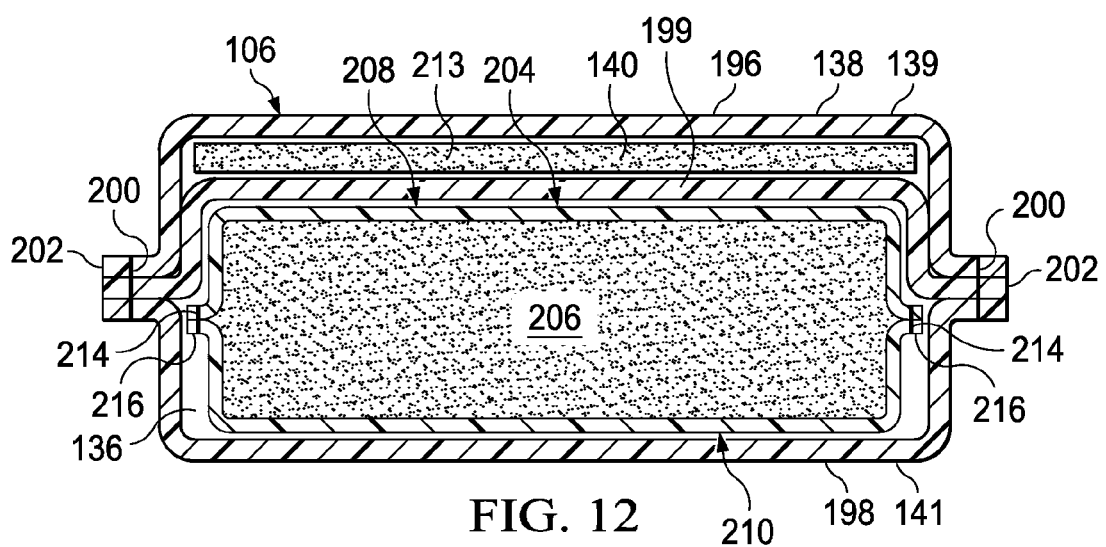
FIG. 12 is a schematic cross section of another illustrative embodiment of the inline storage pouch shown in FIG. 2 taken along line A-A.

Referring now primarily to FIG. 12, another illustrative inline storage pouch 106 is shown in cross section. The inline storage pouch 106 is analogous in most respects to the inline storage pouch 106 of FIGS. 1, 2, and 7-11, and accordingly, some parts are labeled but not further described here. In this illustrative embodiment, a first bypass conduit 140 is formed by using a third wall 199 that together with the first wall 196 forms the first bypass conduit 140. The third wall 199 may be formed from the same materials as the first wall 196. Like in FIG. 11, the first bypass conduit 140 may be at least partially filled with a conduit-manifold material 213. This embodiment allows the first bypass conduit 140 to extend the width of the flexible pouch body 138.

Figure 13:
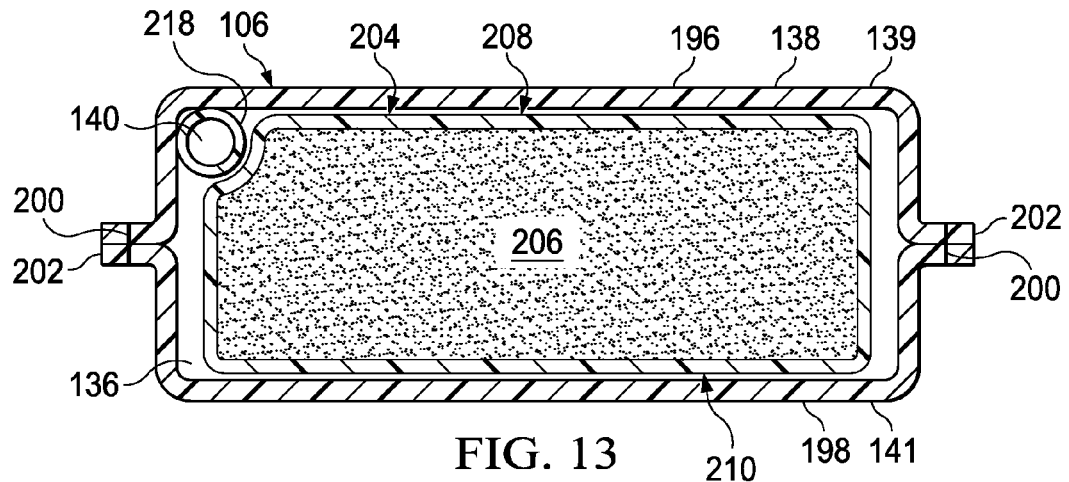
FIG. 13 is a schematic cross section of another illustrative embodiment of the inline storage pouch shown in FIG. 2 taken along line A-A.

Referring now primarily to FIG. 13, another illustrative inline storage pouch 106 is shown in cross section. The inline storage pouch 106 is analogous in most respects to the inline storage pouch 106 of FIGS. 1, 2, and 7-12, and accordingly, some parts are labeled but not further described here. In FIG. 13, the fluid storage material 204 comprises an absorbent member 206 surrounded by a wicking member 208 that has been coated, extruded, or otherwise directly applied onto the exterior of the absorbent member 206.

Figure 14:
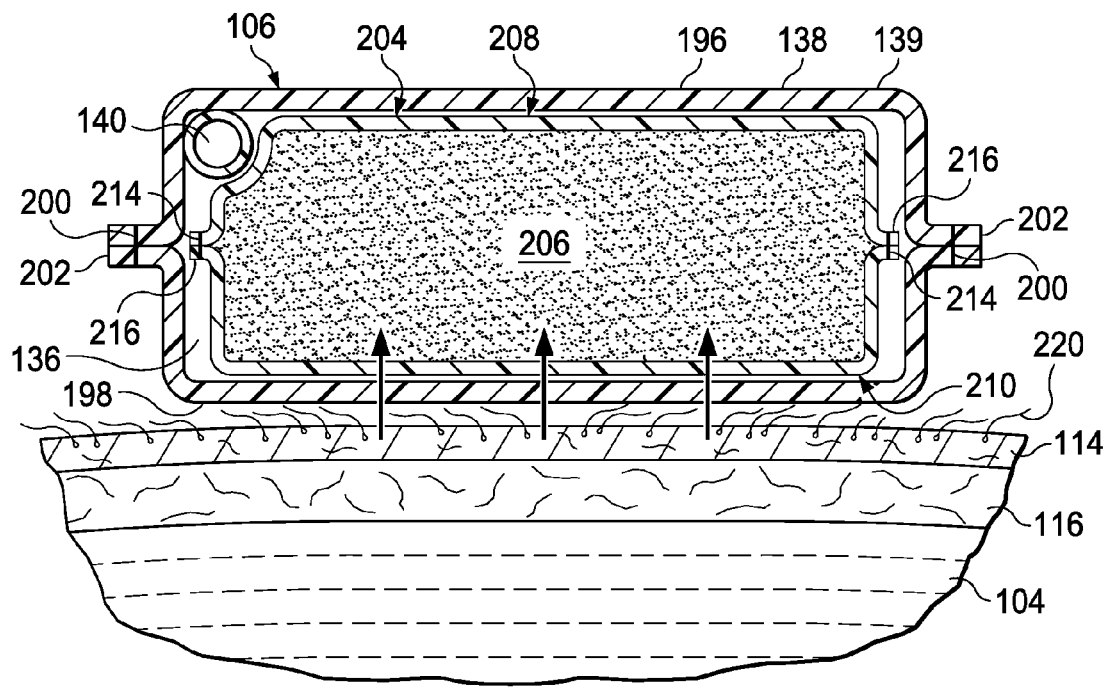
FIG. 14 is a schematic cross section of another illustrative embodiment of the inline storage pouch shown in FIG. 2 taken along line A-A and shown on an animal.
Figure 15:
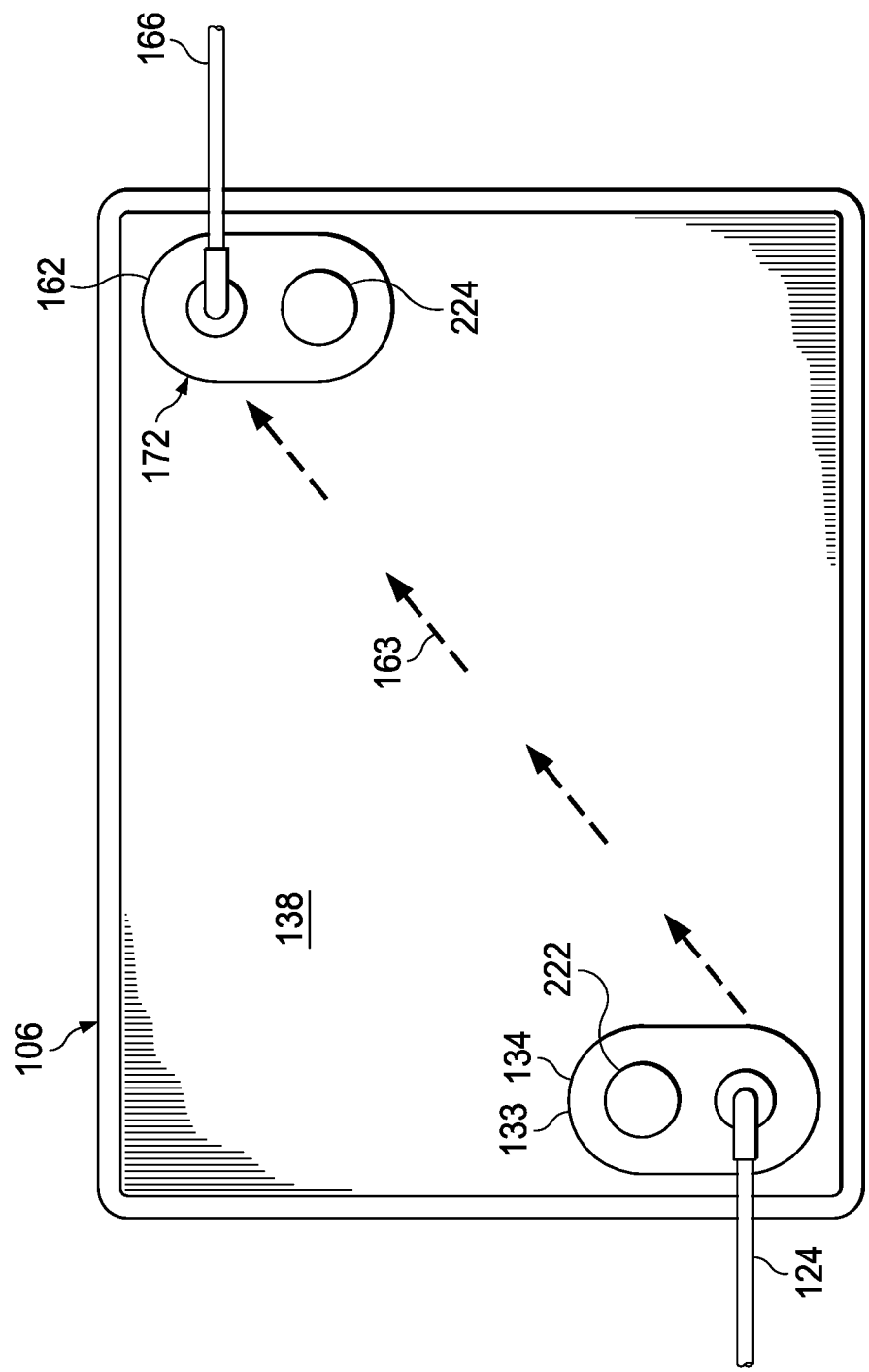
FIG. 15 is a schematic plan view of an illustrative embodiment of an inline storage pouch.

Referring now primarily to FIG. 14, another illustrative inline storage pouch 106 is shown in cross section. The inline storage pouch 106 is analogous in most respects to the inline storage pouch 106 of FIGS. 1, 2, 7-13, and accordingly, some parts are labeled but not further described here. In FIG. 14, the first wall 196 or second wall 198 are formed from a high-vapor-transfer-rate material. The high-moisture-vapor-transfer-rate ("MVTR") material may be formed from any material that allows vapor to egress but not liquids. "Moisture Vapor Transmission Rate" or "MVTR" represents the amount of moisture that can pass through a material in a given period of time. The high-moisture-vapor-transfer-rate material typically has a moisture vapor transmission rate greater than 300 g/m²/24 hours and more typically 1000 g/m²/24 hours or more. The high-moisture-vapor-transfer-rate material allows vapor to egress or diffuse from the interior portion 136, but not liquids.

The high-moisture-vapor-transfer-rate material may comprise one or more of the following: hydrophilic polyurethane, cellulosics, hydrophilic polyamides, an INSPIRE™ 2301 material from Exopack Advanced Coatings of Wrexham, United Kingdom; a thin, uncoated polymer drape; or polyvinyl alcohol, polyvinyl pyrrolidone, hydrophilic acrylics, hydrophilic silicone elastomers and copolymers of these. The INSPIRE™ 2301 illustrative film has an MVTR (inverted cup technique) of 14500-14600 g/m²/24 hours. See www.exopackadvancedcoatings.com. The high-moisture-vapor-transfer-rate materials may have various thicknesses, such as 10 to 40 microns (μm), e.g., 15, 20, 25, 30, 35, 40 microns (inclusive of all numbers in the stated range).

The inline storage pouch 106 has a flexible pouch body 138 with an interior portion 136. Like in FIG. 11, the interior portion 136 is at least partially filled with a storage material 204 that may be formed with a first wicking member 208, an absorbent member 206, and a second wicking member 210. The wicking members 208, 210 may be coupled at their peripheral edges 216 by an attachment 214 (analogous to attachment 200).

The inline storage pouch 106 of FIG. 14 is shown on the animal's epidermis 114. Some clearance between the epidermis 114 and inline storage pouch 106 may be provided by hair 220. Moisture from the animal's epidermis 114 may ingress into the interior portion 136 through the second wall 198, which is formed from a high-moisture-vapor-transfer-rate material. The ingress is due to a moisture imbalance. The moisture enters the second wicking member 210. In addition, moisture may egress the interior portion 136 through the first wall 196, which may also comprise a high-moisture-vapor-transfer-rate material. The egress is due to a moisture imbalance between the interior portion 136 and the external atmosphere across the high-moisture-vapor-transfer-rate material. In another embodiment, a third wicking member may be added on an exterior of the second wall 198 to wick moisture away from the animal's epidermis 114.

In operation according to one illustrative embodiment, the wound dressing 108 is applied to the tissue site 102. The inline storage pouch 106 is positioned at a desired location on the animal 104 or near the animal 104 depending on the application. If applied on the animal 104, the inline storage pouch 106 may be strapped, tapped, or otherwise secured to the animal 104. The inline storage pouch 106 is fluidly coupled to the wound dressing 108 to provide reduced pressure to the wound dressing 108 and to receive wound-site pressure from the tissue site 102. The therapy unit 110 may also be positioned on or near the animal 104. The therapy unit 110 is fluidly coupled to the inline storage pouch 106. The therapy unit 110 provides reduced pressure to the inline storage pouch 106 and receives the wound-site pressure for determining pressure a the tissue site 102. The therapy unit 110 may control the therapy, analyze any blockages, and provide alerts as described further below.

As operation continues, fluids are pulled from the animal 104 into the inline storage pouch 106. The fluid enters the first port 133 and is pulled toward the second port 162. As the fluid is pulled, the fluid is distributed throughout the interior portion 136 and particularly in the fluid storage material 204. As liquids build in the inline storage pouch 106, gases—typically air—continue to move or to manifold through the interior portion 136. The gases may move through the interior portion 136 primarily through the wicking members 208, 210 when included or through space created by the third wicking member 223 or by the offsets 215, 219. Once the inline storage pouch 106 at least partially fills, liquid reaches the second port 162 and the flow is discontinued. In another illustrative embodiment, baffles or internal walls may be added in the interior portion 136 to cause the fluid flow to take a tortuous path between the ports 133, 162.

Referring now primarily to FIGS. 15-17B, another illustrative inline storage pouch 106 is presented. The inline storage pouch 106 is analogous in most respects to the inline storage pouch 106 of FIGS. 1, 2, and 7-14, and accordingly, some parts are labeled but not further described here. In addition, components referenced but not explicitly shown are analogous to those previously presented. In this illustrative embodiment, the flexible pouch body 138 includes a first port 133 having a first reduced-pressure indicator 222 and a second port 162 having a second reduced-pressure indicator 224. The ports 133, 162 are shown on the same side of the flexible pouch body 138, but it should be understood that one or both of the ports 133, 162 may be located on the opposite side as shown in other figures herein.

Figure 16:
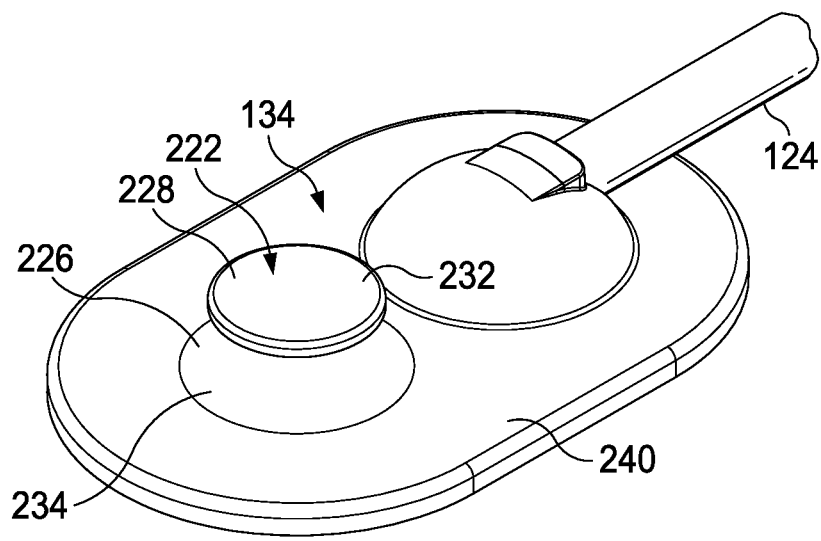
FIG. 16 is a schematic, perspective view of, inter alia, a reduced-pressure indicator.

The first reduced-pressure indicator 222 may be fluidly coupled to the interior portion 136 of the flexible pouch body 138 proximate to the first port 133 or as an aspect of the first port 133. The first reduced-pressure indicator 222 may be included as an aspect of the patient-port interface 134 as shown in FIG. 16. The first reduced-pressure indicator 222 provides a visual indication of whether or not the first reduced-pressure indicator 222 experiences a reduced pressure greater than a first threshold.

Similarly, the second reduced-pressure indicator 224 may be fluidly coupled to the interior portion 136 of the flexible pouch body 138 proximate to the second port 162 and may be part of the device-port interface 172. The second reduced-pressure indicator 224 provides a visual indication of whether or not the second port 162 experiences a reduced pressure greater than a second threshold, which may be the same as the first threshold.

Referring now primarily to FIGS. 16-17, the reduced-pressure indicators 222, 224 are described. The reduced-pressure indicators 222, 224 are analogous to one another. The reduced-pressure indicators 222, 224 may each be formed with a moving member 226 adapted to move when reduced pressure exceeds a threshold pressure ($P_t$). The reduced-pressure indicators 222, 224 have a visual indicator 228 associated with the moving member 226. In one embodiment, the visual indicator 228 is an indicator member 230 or portion, such as a disk-shaped member 232 (or button), or a member of any shape that signifies a changed state with respect to pressure.

The moving member 226 may be a collapsible wall 234 that has a first end 236 and a second end 238. The first end 236 may be coupled to the indicator member 230. The second end 238 may be coupled to a base 240. The collapsible wall 234 and indicator member 230 form a pressure vessel with base 240. The collapsible wall 234 may have a convex interior surface and may include baffles or other features to assist in collapsing at the threshold pressure.

Figure 17A:
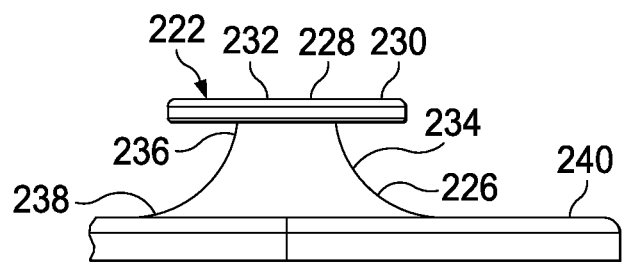
FIG. 17A is a schematic elevation view of the reduced-pressure indicator of FIG. 12 shown in an extended position.
Figure 17B:
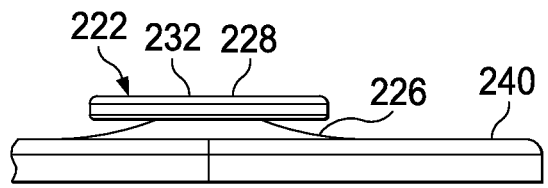
FIG. 17B is a schematic elevation view of a portion of the reduced-pressure indicator of FIG. 12 shown in a retracted position.

When reduced pressure delivered to the interior portion 136 exceeds the threshold pressure ($P_t$), the collapsible wall 234 collapses (alone or with movement in the base 240) and causes the visual indicator 228 to go from a first position, e.g., an extended position, to a second position, e.g., a retracted position, as shown in FIGS. 17A and 17B, respectively. The collapsible walls 234 of the reduced-pressure indicator may be sized and shaped to collapse or move the indicator member 230 to be substantially flush or against the base 240 when the threshold reduced pressure ($P_t$) is achieved. When the pressure rises (with reference to absolute pressure) above the threshold reduced pressure ($P_t$), the collapsible wall 234 returns to the extended position. In other words, the reduced pressure causes the reduced-pressure indicator to collapse as long as there is adequate reduced pressure.

The thickness of the collapsible wall 234, wall material stiffness, and wall geometry are variables that impact the pressure at which the collapsible wall 234 collapses. The rigidity of the base 240 may also be a factor. While the wall thickness of the collapsible wall 234 may be determined using finite element analysis, it may be necessary to empirically determine the wall thickness to achieve movement at the threshold pressure ($P_t$). In some embodiments, the collapsible wall 234 may be designed so that the collapsible wall 234 collapses by sudden buckling as the threshold pressure ($P_t$) is crossed, providing a binary indication. The reduced-pressure indicator 222, 224 may be formed on the base 240 with other aspects of the patient-port interface 134 or device-port interface 172.

The reduced-pressure indicator 222, 224, interfaces 134, 172, and base 240 may be formed from a medical-grade, soft polymer or other pliable material, such as one or more of the following: polyurethane, polyethylene, polyvinyl chloride (PVC), fluorosilicone, ethylene-propylene, DEHP-free PVC, or other material. The components may be cast, or extruded, and may be formed as an integral unit.

In operation, if the pressure sensing unit 170 shows a lack of reduced pressure at the tissue site 102, the user may analyze the situation using the reduced-pressure indicators 222, 224. If pressure is being received at the first reduced-pressure indicator 222, i.e., the indicator member 230 shows that the collapsible wall 234 is still collapsed, then a problem exists between the tissue site 102 and the inline storage pouch 106. If the first reduced-pressure indicator 222 shows inadequate pressure, i.e., the indicator member 230 shows that the collapsible wall 234 is no longer collapsed and if the second reduced-pressure indicator 224 shows adequate pressure, i.e., the indicator member 230 shows that the collapsible wall 234 is still collapsed, then a problem exists within the inline storage pouch 106. If the second reduced-pressure indicator 224 shows inadequate pressure, i.e., the indicator member 230 shows that the collapsible wall 234 is no longer collapsed, then a problem exists with either the filter 194 being occluded or somewhere between the inline storage pouch 106 and the reduced-pressure source 112.

Figure 18:
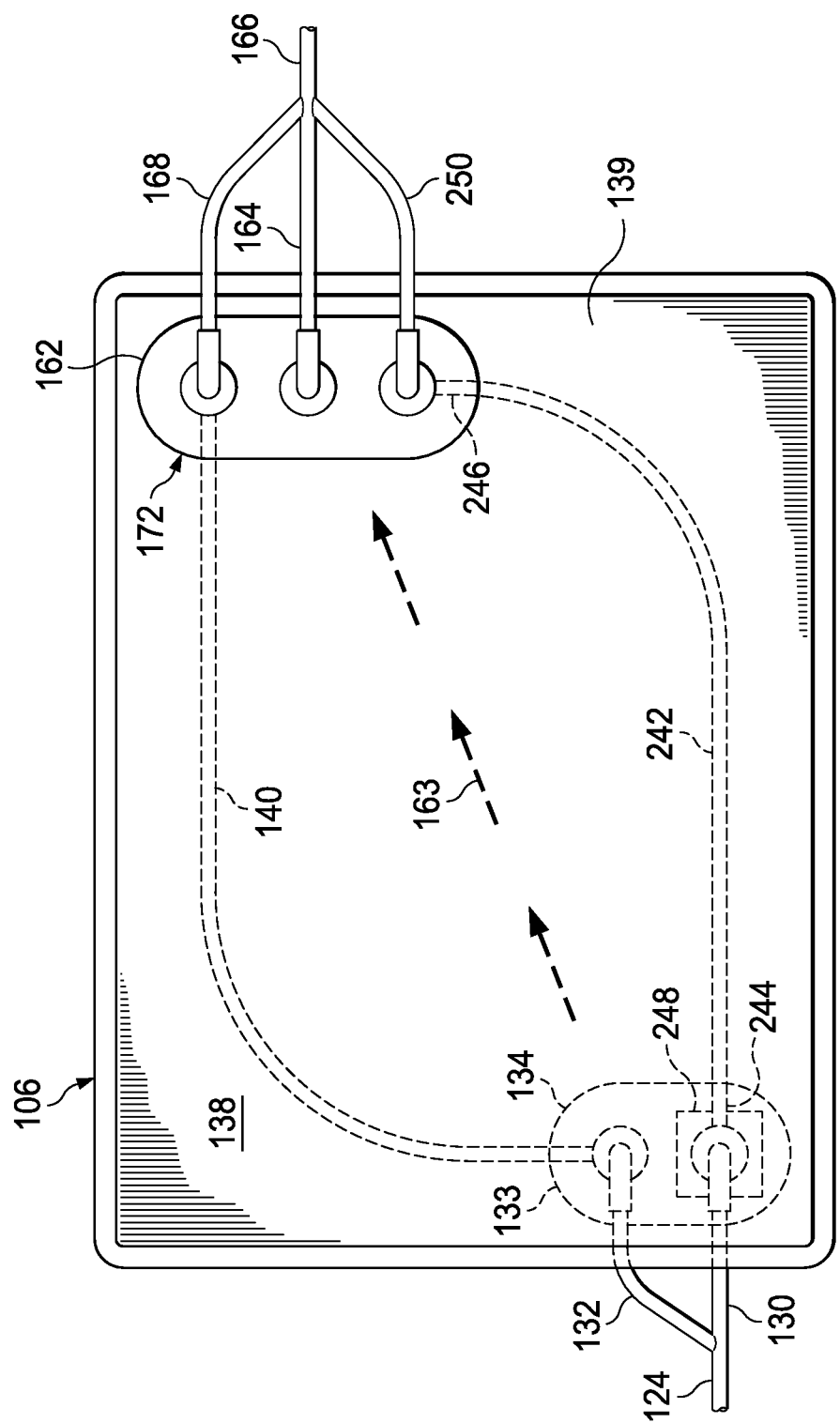
FIG. 18 is a schematic plan view of an illustrative embodiment of an inline storage pouch.

Referring now primarily to FIG. 18, another illustrative embodiment of an inline storage pouch 106 is presented. The inline storage pouch 106 is analogous in most respects to the inline storage pouch 106 of FIGS. 1, 2, and 7-14, and accordingly, some parts are labeled but not further described here. In addition, components referenced but not explicitly shown are analogous to those previously presented. The illustrative embodiment of FIG. 18 includes a second bypass conduit 242 fluidly disposed within and fluidly isolated from the interior portion 136 of the flexible pouch body 138. The second bypass conduit 242 has a first end 244 and a second end 246. The first end 244 of the second bypass conduit 242 may be fluidly coupled to the interior portion 136 of the flexible pouch body 138 proximate to the first port 133 at a first pressure-sensing pad 248. In addition to the second reduced-pressure lumen 164 and second sensing lumen 168, the second multi-lumen conduit 166 also includes a first pouch-pressure-sensing conduit 250. The second end 246 of the second bypass conduit 242 may be fluidly coupled to the first pouch-pressure-sensing conduit 250. The first port 133 may be located on the second, animal-facing side of the flexible pouch body 138 and the second port 162 may be on the first side 139. In another illustrative embodiment, the ports 133, 162 may be on the same side or reverse sides as to what is described herein above Still with reference to FIG. 18 and to a lesser extent to FIG. 2, the pressure sensing unit 170 may be fluidly coupled to the second sensing lumen 168 and separately to the first pouch-pressure-sensing conduit 250. Thus, therapy unit 110, which also may include a microprocessor 253, is able to determine the pressure at the tissue site 102 and also in the interior portion 136 of the flexible pouch body 138 proximate to the first port 133. The therapy unit 110 may check the pressure proximate the first port 133 (in the first pressure-sensing pad 248) proactively or if inadequate pressure, i.e., below a threshold, is determined at the tissue site 102. If adequate pressure exists in the first pressure-sensing pad 248 but not at the tissue site 102, the therapy unit 110 may provide an alert that a blockage exists between the inline storage pouch 106 and the tissue site 102. If inadequate pressure exists at the first pressure-sensing pad 248, the therapy unit 110 may signal that the inline storage pouch 106 is full or block exists between the inline storage pouch 106 and the reduced-pressure source 112.

Figure 19:
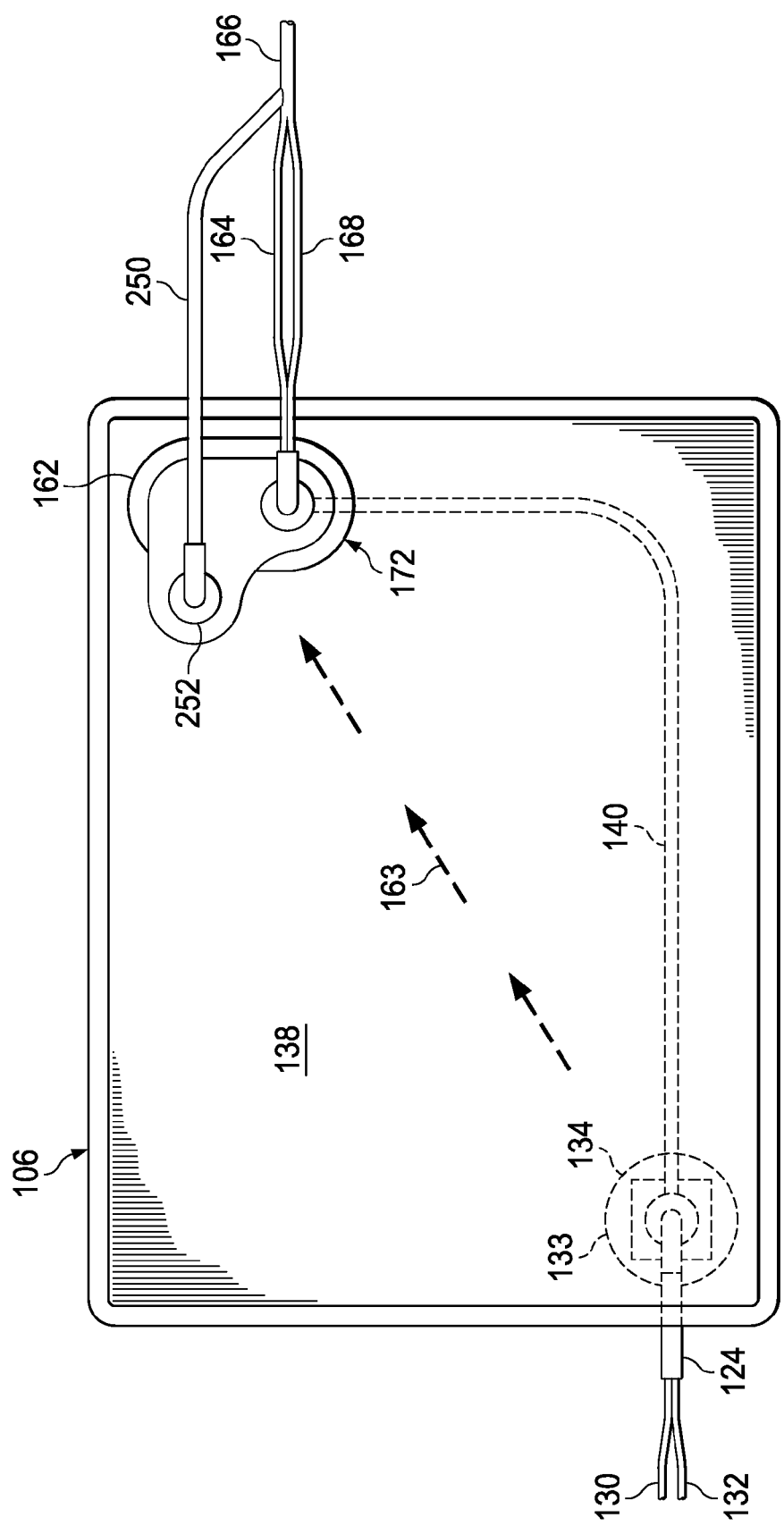
FIG. 19 is a schematic plan view of an illustrative embodiment of an inline storage pouch.

Referring now primarily to FIG. 19 and to a lesser extent FIG. 2, another illustrative embodiment of an inline storage pouch 106 is presented. The inline storage pouch 106 is analogous in most respects to the inline storage pouch 106 of FIGS. 1, 2, 7-14, and 18, and accordingly, some parts are labeled but not further described here. In addition, components referenced but not explicitly shown are analogous to those previously presented.

In this embodiment, a second pressure-sensing pad 252 has been coupled proximate to the second port 162. The second pressure-sensing pad 252 includes a filter element (not explicitly shown) that becomes occluded when saturated with liquid. The second pressure-sensing pad 252 may be fluidly coupled to the interior portion 136 of the flexible pouch body 138 proximate to the second port 162. As before, the second multi-lumen conduit 166 further includes a first pouch-pressure-sensing conduit 250 fluidly coupled to the pressure sensing unit 170 of the therapy unit 110. When the therapy unit 110 detects that the second pressure-sensing pad 252 is occluded, the therapy unit 110 may signal that the inline storage pouch 106 is full.

Figure 20:
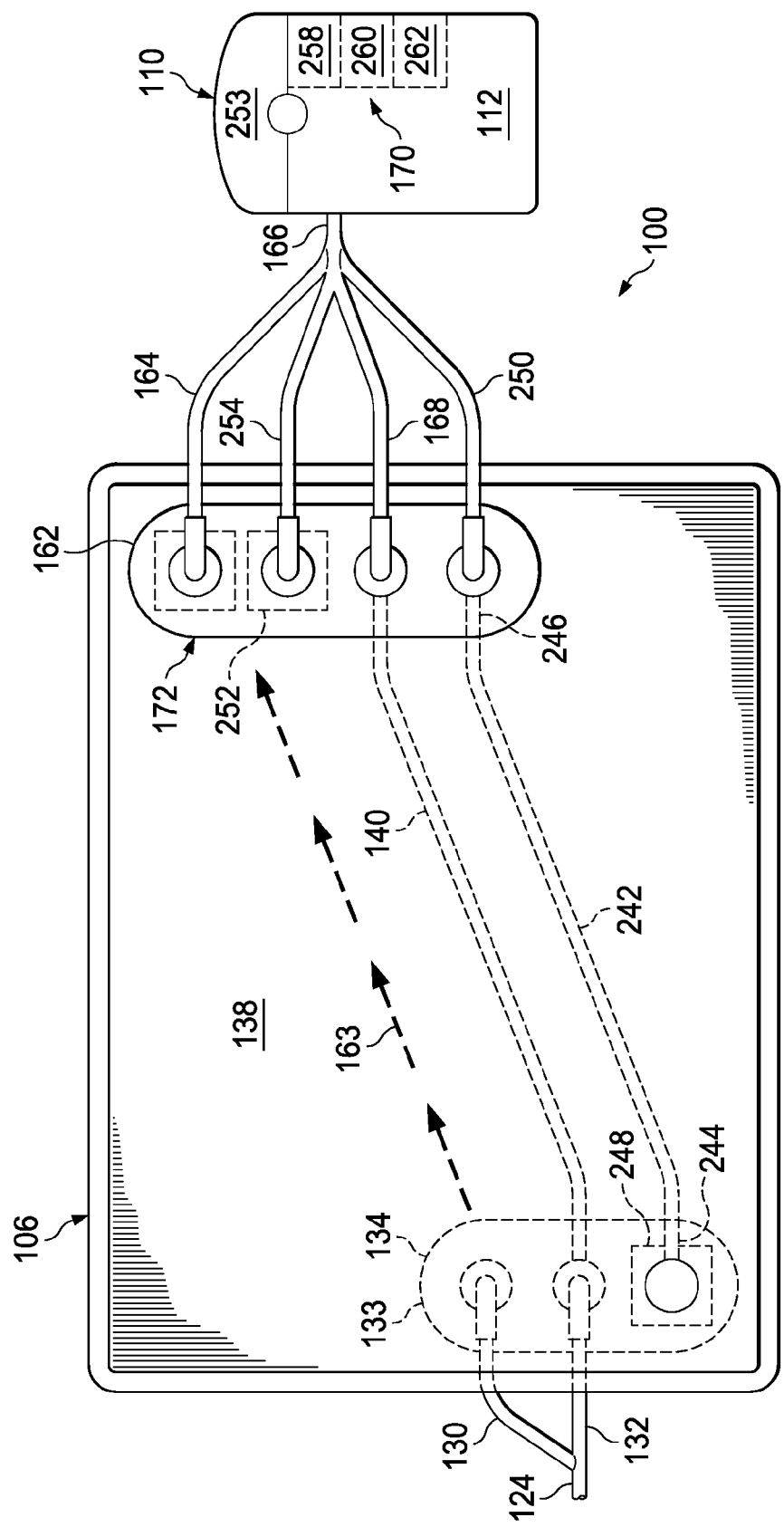
FIG. 20 is a schematic plan view of an illustrative embodiment of an inline storage pouch.

Referring now primarily to FIG. 20 and to a lesser extent FIG. 2, another illustrative embodiment of an inline storage pouch 106 is presented. The inline storage pouch 106 is analogous in most respects to the inline storage pouch 106 of FIGS. 1, 2, 7-14, and 18-19 and accordingly, some parts are labeled but not further described here. In addition, components referenced but not explicitly shown are analogous to those previously presented.

In this embodiment, the inline storage pouch 106 includes the second bypass conduit 242 as in FIG. 18 fluidly coupled to the interior portion 136 of the flexible pouch body 138 proximate to the first port 133. The second bypass conduit 242 may also be fluidly coupled to the first pouch-pressure-sensing conduit 250. The inline storage pouch 106 also includes a second pressure-sensing pad 252 like in FIG. 19 fluidly coupled to the interior portion 136 of the flexible pouch body 138 proximate to the second port 162 and to a second pouch-pressure-sensing conduit 254. The second pouch-pressure-sensing conduit 254 may be fluidly coupled to the second pressure-sensing pad 252 and to a therapy unit 110.

The portion of the system 100 shown in FIG. 20 includes the therapy unit 110. The therapy unit 110 includes the reduced-pressure source 112 and pressure sensing unit 170. The pressure sensing unit 170 includes a first pressure sensing device 258, a second pressure sensing device 260, and a third pressure sensing device 262. The first pressure sensing device 258 is fluidly coupled to the pressure-assessment conduit 128 of the reduced-pressure interface 122 for determining a wound-site pressure, i.e., the pressure at the tissue site 102. The second pressure sensing device 260 may be fluidly coupled to the first pressure-sensing pad 248 for determining pressure proximate the first port 133. The third pressure sensing device 262 may be fluidly coupled to the second pressure-sensing pad 252 for determining pressure at the second port 162.

More particularly, the first pressure sensing device 258 may be fluidly coupled to the second sensing lumen 168 of the second multi-lumen conduit 166. The second sensing lumen 168 may also be fluidly coupled to the first bypass conduit 140 and to the sensing lumen 132 of the first multi-lumen conduit 124. The sensing lumen 132 may be fluidly coupled to the pressure-assessment conduit 128. The second pressure sensing device 260 may be fluidly coupled to the first pouch-pressure-sensing conduit 250. The first pouch-pressure-sensing conduit 250 may be fluidly coupled to the second bypass conduit 242. The second bypass conduit 242 may be fluidly coupled to first pressure-sensing pad 248 proximate to the first port 133. The third pressure sensing device 262 may be fluidly coupled to the second pouch-pressure-sensing conduit 254. The second pouch-pressure-sensing conduit 254 may be fluidly coupled to the second pressure-sensing pad 252.

Figure 21:
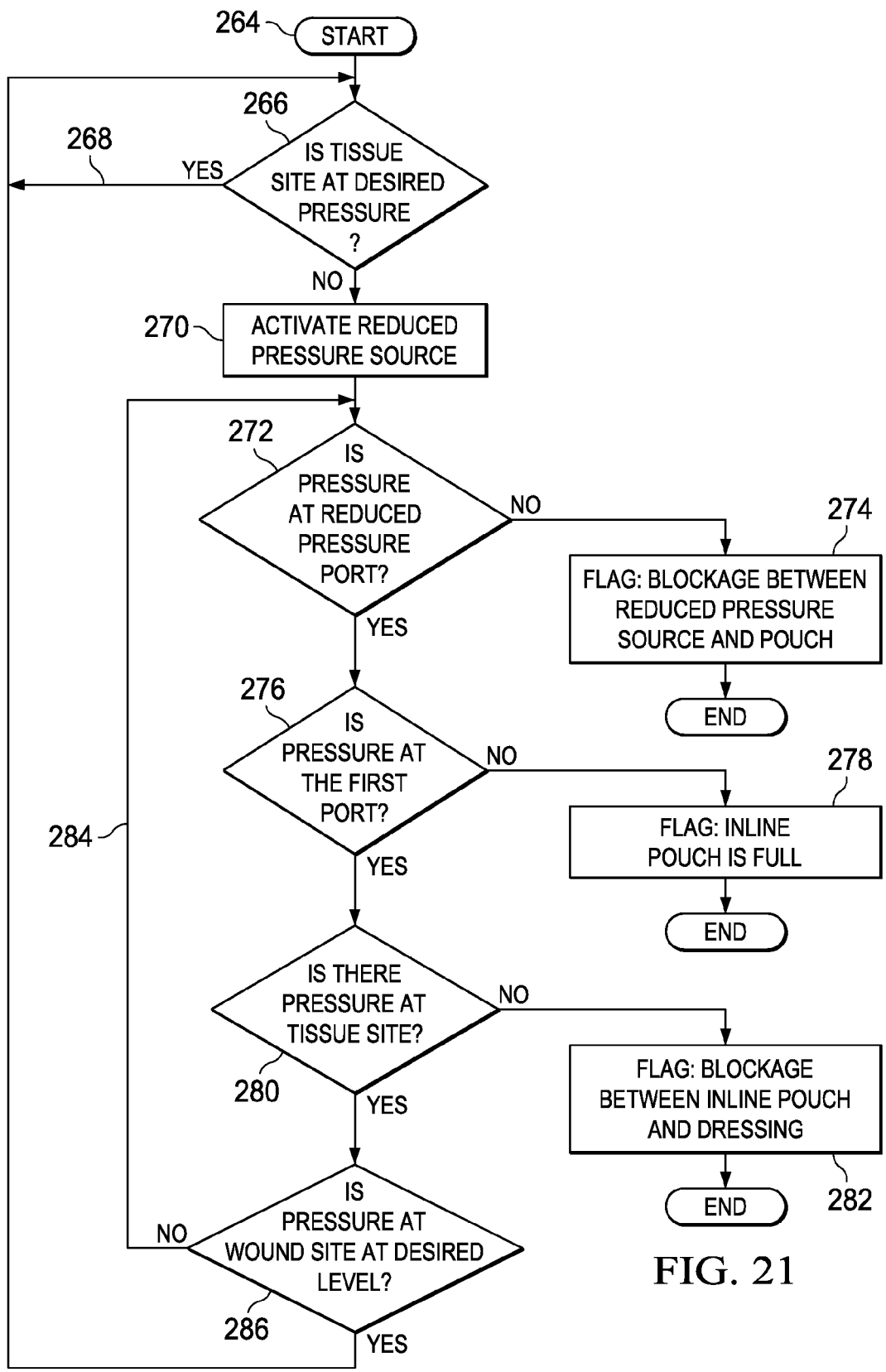
FIG. 21 is a schematic, illustrative flow diagram of steps that may be performed using a microprocessor in an illustrative system for treating a tissue site on an animal with reduced pressure that involves storing liquids in an inline storage pouch.

With the portion of the system 100 shown in FIG. 20, the therapy unit 110 may pinpoint the location (or at least give an area) of blockage or may indicate that the inline storage pouch 106 is full. Referring now primarily to FIG. 21, one possible logic flow for operation of the system in FIG. 20 is presented. The process begins at step 264 and the first interrogatory box 266 inquires as to whether or not the desired pressure is being realized at the tissue site 102. The microprocessor 253 may determine this by comparing the pressure determined by the first pressure sensing device 258 with a selected pressure threshold. If the interrogatory is affirmative, the process continues back along path 268. If not, the microprocessor 253 may activate the reduced-pressure source 112 at step 270 to provide reduced pressure. Optionally a certain amount of time may be required before moving beyond step 270 and the interrogatory box 266 may be revisited.

With inadequate pressure existing, the interrogatory box 272 is reached and calls for the pressure to be checked at the second port 162 by the second pressure-sensing pad 252. The microprocessor 253 receives the pressure from the third pressure sensing device 262. If there is not a reduced pressure greater (i.e., more reduced with respect to absolute pressure) than a threshold reduced pressure at the second port 162, a flag is raised at step 274 that a blockage exists between the reduced-pressure source 112 and the inline storage pouch 106. If adequate pressure is at the second port 162, the problem must be elsewhere and the process continues to interrogatory box 276. Interrogatory box 276 inquires as to the pressure at the first port 133. The microprocessor 253 receives the pressure from the second pressure sensing device 260. If the pressure is inadequate, step 278 is reached an alert posted that the pouch is full or blocked.

If pressure exists at the first port 133 but not at the tissue site 102, which is the question of interrogatory box 280, an alert is issued at step 282 that a blockage exists between the inline storage pouch 106 and the wound dressing 108. If pressure exists at the tissue site 102, but is not adequate, another round of analysis may occur as suggested by path 284. A counter or chronograph may be included to limit the number of times through the cycle. Thus, after a maximum count or maximum time, an error flag may be provided. If adequate pressure is now realized at the tissue site 102, the answer to interrogatory box 286 is positive and the process continues from interrogatory box 286 to interrogatory box 266. This is one illustrative process and many others may be used. Those skilled in the art will understand various ways to implement the functionality in hardware or software. In addition, portions of this process may be used separately.

Referring now primarily to FIGS. 22-27, another illustrative embodiment of an inline storage pouch 300 is presented. The inline storage pouch 300 is analogous in many respects to the inline storage pouch 106 of the previous figures. The inline storage pouch 300 includes a pouch connector 302. The inline storage pouch 300 may be used as part of a system, e.g., system 100 of FIG. 1, to treat a tissue site on an animal.

The inline storage pouch 300 includes a flexible pouch body 304. The flexible pouch body 304 is formed with a first wall 306, a second wall 308, and a partitioning wall 310. The walls 306 and 308 form an interior portion partitioned by the partitioning wall 310 to form a first chamber 312 and a second chamber 314. The walls may be formed from any liquid-impermeable, flexible material, for example, polyurethane or any of those materials previously mentioned for the wall 196. The flexible pouch body 304 has a proximal end 316 and a distal end 318. A longitudinal axis extends generally between the proximal end 316 and the distal end 318.

A first manifolding material 320 is disposed within the first chamber 312. The first manifolding material 320 may be formed from the same materials as conduit-manifold material 213, e.g., BASF Luquafleece 402C or an analogous material.

A fluid storage material 321 is disposed within the second chamber 314. The fluid storage material 321 may be surrounded by a wicking material 322. The wicking material 322 may be one or more of the materials mentioned for wicking material 208, e.g., Libeltex TDL2 80 gsm or an analogous material. The wicking material 322 may be two separate pieces of material that are welded or otherwise coupled at their peripheral edges 324 to form a "tea bag" like arrangement containing the fluid storage material 321. The wicking material 322 may include one or more apertures, e.g., aperture 323 to facilitate a portion of the pouch connector 302 to extend therethrough.

A second manifolding material 326 may also be disposed within the second chamber 314. The second manifolding material 326 may be the same as first manifolding material 320, but in another embodiment is shown as a plastic layer 328 having offsets 330. The offsets 330 may be in the range 0.25-0.5 mils from a base of the plastic layer. The offsets 330 may be formed by injection molding the plastic layer 328 with offsets or vacuum forming. The offsets 330 may be ridges a shown, pegs, or any spacer. The second manifolding material 326 functions to ensure that the exudate collecting area (chamber) remains open. The offsets 330 may be the same or analogous to offsets 215, 219.

The pouch connector 302 is coupled to the flexible pouch body 304 proximate the proximal end 316 but could be placed at other locations. The pouch connector 302 receives fluids from the animal and delivers the fluids to the second chamber 314. The pouch connector 302 also fluidly couples reduced pressure received from a reduced-pressure source to the first chamber 312.

The pouch connector 302 includes a connector body 332 formed with an exudate chamber 334. The exudate chamber 334 has an intake port 336 for receiving the fluids from the animal and an outlet 338 for discharging the fluids from the animal. The intake port 336 may comprise a first tube connector 337 for coupling to a first conduit 339. The first tube connector 337 may include a tube lock 372. The first conduit 339 may be a multi-lumen conduit having a first reduced-pressure lumen 341 and a first pressure-sensing lumen 343. A displacement conduit 340 is fluidly coupled to the outlet port 338 and the second chamber 314 for delivering the fluids from the exudate chamber 334 to the second chamber 314. The displacement conduit 340 may be a tube or a hollow offset that is open or the like.

The connector body 332 is also formed with a reduced-pressure chamber 342. The exudate chamber 334 and reduced-pressure chamber 342 are fluidly isolated from each other within the pouch connector 302 by a portion of the connector body 332. The reduced-pressure chamber 342 has an intake port 344 for receiving fluids from the first chamber 312 and an outlet port 346 for discharging fluids. The outlet port 346 of the reduced-pressure chamber 342 is for receiving the reduced pressure from the reduced-pressure source. The outlet port 346 may comprise a tube connector 348 that couples to a second conduit 350 that is fluidly coupled to a reduced-pressure unit or source, e.g., therapy unit 110 in FIG. 2. The second conduit 350 may be a multi-lumen conduit that has a reduced-pressure lumen for delivering reduced pressure ultimately to the first chamber and a second pressure-sensing lumen for receiving reduced pressure ultimately from the first reduced-pressure sensing lumen via the pouch connector 302.

The connector body 332 may also includes a plurality of offsets 352 on the connector body 332 proximate to the intake port 344 of the reduced-pressure chamber 342. The offsets 352 may be in the range of 0.5 mils to several mils. The offsets 352 function to ensure fluid flow proximate to the intake port 344 in the first chamber 312.

The intake port 336 of the exudate chamber 334 may be substantially parallel to the outlet port 346 of the reduced-pressure chamber 342. The flexible pouch body 304 has a longitudinal axis (substantially parallel to section line 23-23 in FIG. 22) that may be substantially parallel to the axis of the intake port 336 of the exudate chamber 334 and may be perpendicular to the axis of the displacement conduit 340.

The partitioning wall 310 of the flexible pouch body 304 is formed with an exudate aperture 354 for receiving a portion of the pouch connector 302, e.g., the displacement conduit 340, into the second chamber 314. The partitioning wall 310 may be coupled to the displacement conduit 340 to form a fluid seal to prevent fluid from entering the first chamber 312 from the second chamber at that point. The coupling may be formed using any coupling technique, e.g., glue, epoxy, UV glue, welds, bonds, or other techniques.

A first connector aperture 355 may be formed in the first manifold material 320 on the proximal end 316. The exudate aperture 354 is formed on the proximal end of the partitioning wall 310 and is sized and configured to align with exudate aperture 354. At the other end, the distal end of the partitioning wall 310, a return aperture 356 is formed for allowing fluid flow from the second chamber 314 into the first chamber 312. Stated another way, reduced pressure may flow from the first chamber 312 through the return aperture 356 to the second chamber 314. A primary filter 358, e.g., a hydrophobic filter, covers the return aperture 356 to inhibit liquids from entering the first chamber 312. A secondary filter 360 may also be included that covers the fluid path of the return aperture 356. A piece of manifolding material 362 may be used to separate the primary filter 358 and the secondary filter 360. An apron of polyurethane 364 or other material may be used to secure secondary filter 360 and the manifolding material 362 to a first side of the partitioning wall 310. A charcoal filter or other odor filter may be added as well.

A second connector aperture 366 may be formed in the first wall 306 to allow a portion of the pouch connector 302 to extend through the second connector aperture 366. The second connector aperture 366 may facilitate coupling a portion of the first wall 306 to a base portion 368 of the pouch connector 302.

Figure 24:
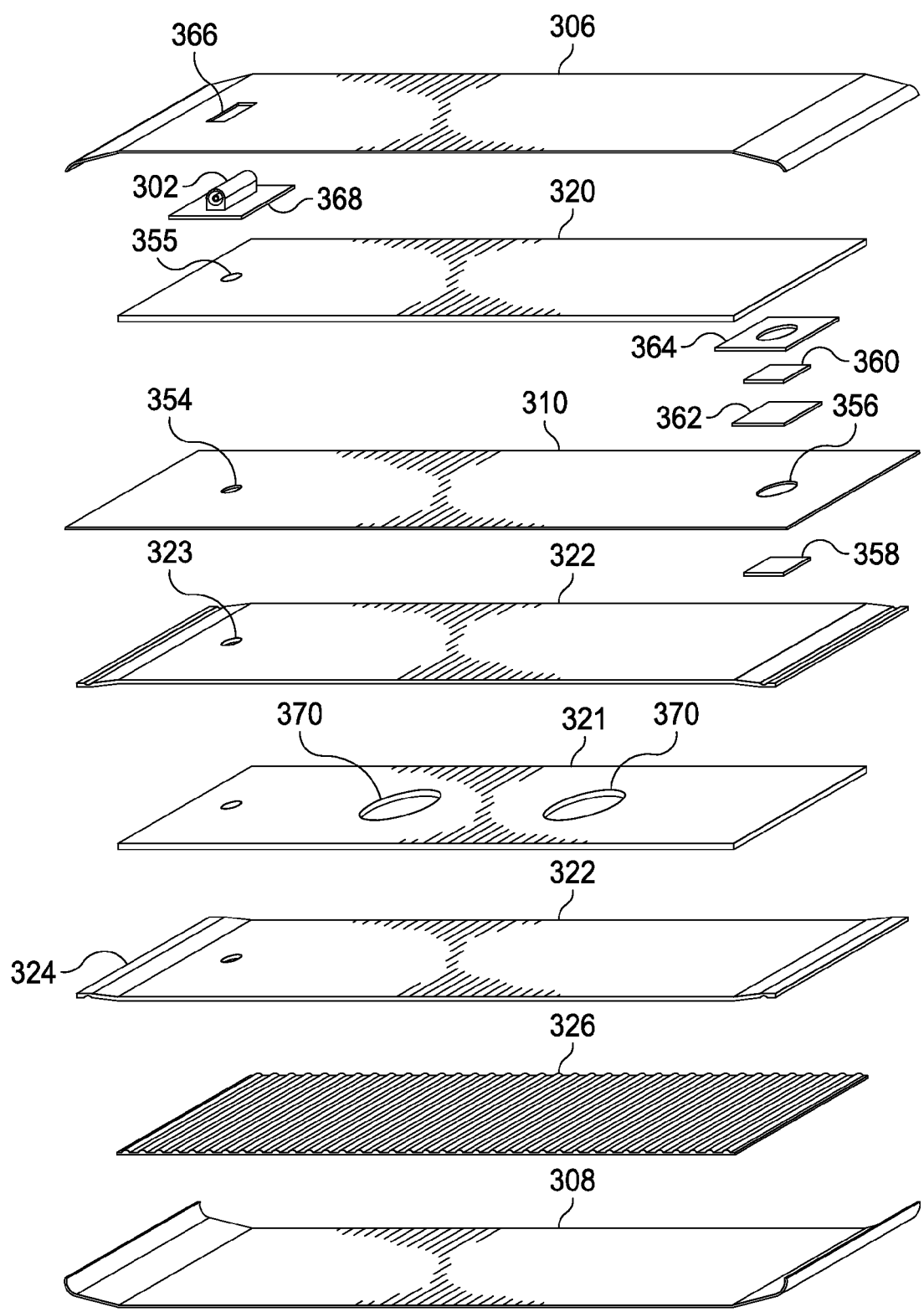
FIG. 24 is a schematic, exploded perspective view of the inline storage pouch of FIGS. 22-23.
Figure 25:
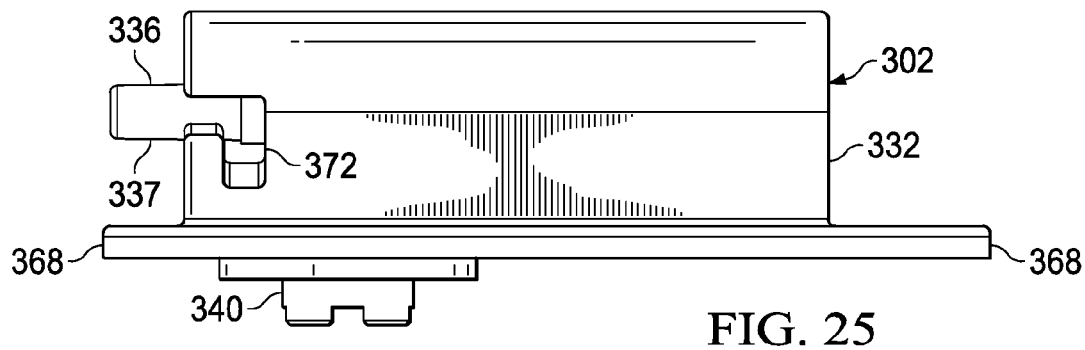
FIG. 25 is a schematic elevation view of an illustrative embodiment of a pouch connector shown in FIGS. 21-24.

As shown best in FIG. 24, the fluid storage material 321 may have one or more apertures 370. The apertures 370 facilitate coupling of a portion of the partitioning wall 310 to the second wall 314 at locations between the proximal and distal ends. While not explicitly shown, apertures in the wicking material 322 may be formed that align with the apertures 370.

Figure 22:
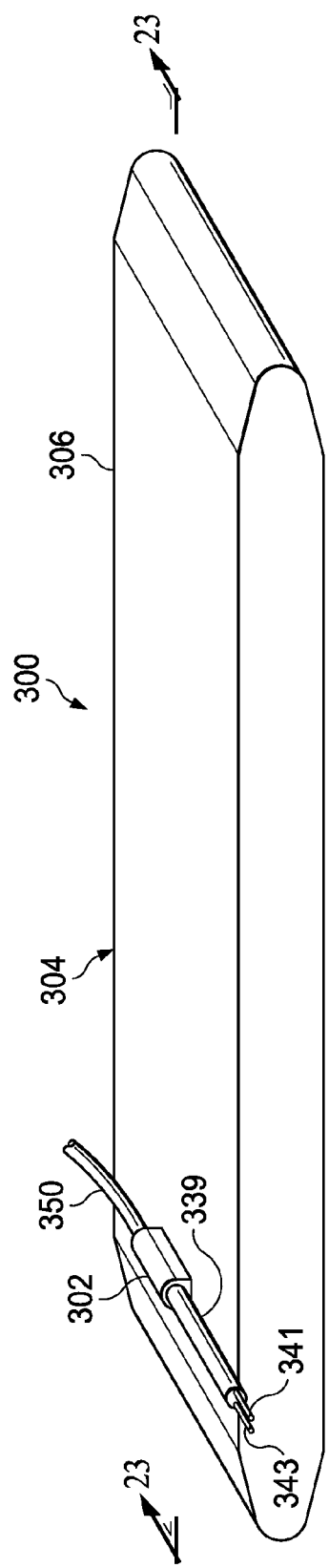
FIG. 22 is a schematic, perspective view of an illustrative inline storage pouch for use with a system such as that shown in FIG. 1.
Figure 23:
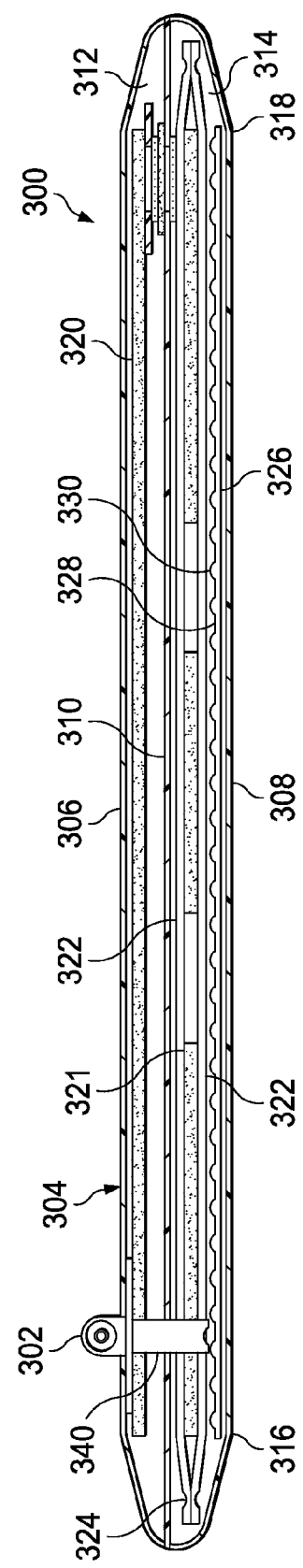
FIG. 23 is a schematic cross-sectional view of the inline storage pouch of FIG. 22.
Figure 26:
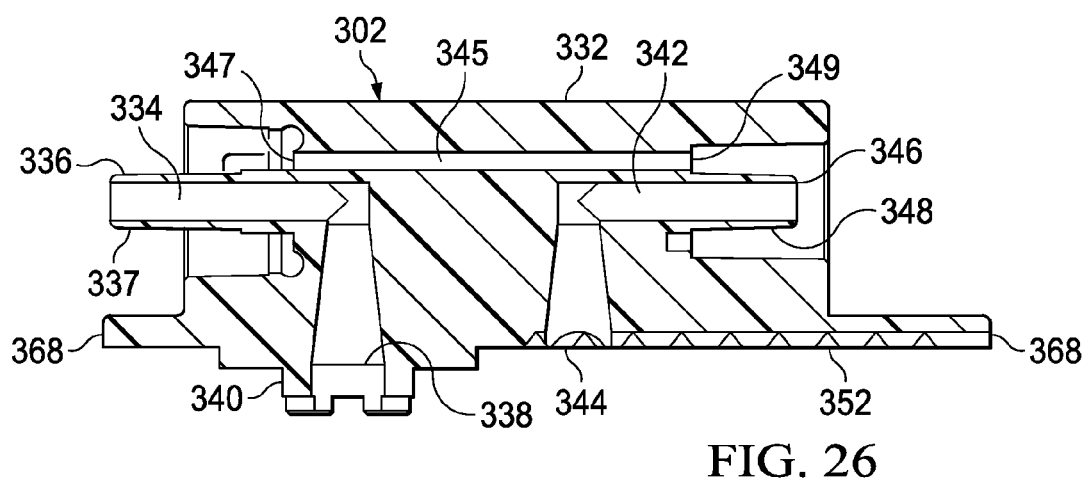
FIG. 26 is a schematic cross-sectional view of the pouch connector of FIG. 25.
Figure 27:
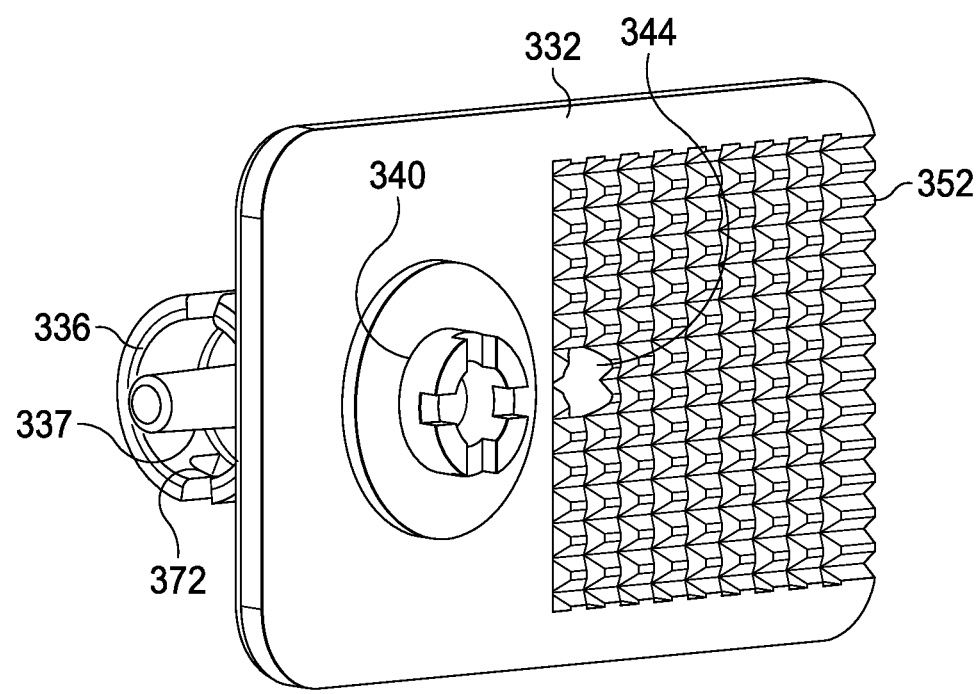
FIG. 27 is a schematic, perspective view showing primarily a second, tissue-facing side of the pouch connector of FIGS. 25-26.

Referring primarily to FIGS. 22 and 26, the pressure-sensing lumen 343 of first conduit 339 is fluidly coupled to a pressure-sensing channel 345 at a first end 347. The pressure-sensing channel 345 is formed in the connector body 332 of the pouch connector 302. The pressure-sensing channel 345 allows a fluid to be communicated through the pouch connector 302. A second end 349 of the pressure-sensing channel 345 is fluidly coupled to a pressure-sensing lumen (not explicitly shown) in the second conduit 350 that is fluidly coupled to a reduced-pressure unit, e.g., therapy unit 110 in FIG. 2, that thereby monitors the pressure at the tissue site on the animal.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment. For example, the bypass conduit shown in one embodiment, e.g., 140 in FIG. 7, may be used in FIG. 11 or vice versa.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, features of any of the embodiments described above may be combined with features of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. An inline storage pouch for use with body fluids from an animal, the inline storage pouch comprising:
    a flexible pouch body having an interior portion;
    a fluid storage material disposed within the interior portion;
    a first port formed on the flexible pouch body configured to connect to a first multi-lumen conduit extending from the flexible pouch body to the animal, the first multi-lumen conduit having at least one sensing lumen and at least one reduced pressure lumen;
    a second port comprising a device interface formed on the flexible pouch body and configured to fluidly connect to a second multi-lumen conduit extending from the flexible pouch body to a reduced pressure source, the second multi-lumen conduit having at least one sensing lumen and at least one reduced pressure lumen, the device interface comprising:
        a device-port body having at least one offset formed on a second, pouch-facing side of the device-port body for providing a filter space; and
    a first bypass conduit disposed within and fluidly isolated from the interior portion of the flexible pouch body, the first bypass conduit having a first end and a second end, the first end of the first bypass conduit fluidly coupled to the at least one sensing lumen of the first multi-lumen conduit and the second end of the first bypass conduit fluidly coupled to the at least one sensing lumen of the second multi-lumen conduit.

2. The inline storage pouch of claim 1, wherein the first port comprises a patient-port interface coupled to the flexible pouch body, the patient-port interface comprising:
    a patient-port body having a first side and a second, pouch-facing side;
    wherein the patient-port body comprises a first hollow attachment connector for mating with the at least one reduced pressure lumen;
    a first fluid outlet formed on the patient-port body and fluidly coupled to the first hollow attachment connector;
    wherein the patient-port body comprises a second hollow attachment connector for mating with the at least one sensing lumen;
    a first pressure-sensing connector fluidly coupled to the second hollow attachment connector, the pressure-sensing connector for coupling to the first bypass conduit; and
    a first plurality of offsets formed on the second, pouch-facing side of the patient-port body for providing flow space.

3. The inline storage pouch of claim 1, wherein the device-port interface further comprises:
    the device-port body having a first side and the second, pouch-facing side;
    wherein the device-port body comprises a third hollow attachment connector for mating with the at least one reduced pressure lumen;
    a fluid inlet formed on the device-port body and fluidly coupled to the third hollow attachment connector;
    wherein the device-port body comprises a fourth hollow attachment connector for mating with the at least one sensing lumen; and
    a second pressure-sensing connector fluidly coupled to the fourth hollow attachment connector, the second pressure-sensing connector for coupling to the first bypass conduit.

4. The inline storage pouch of claim 1, wherein the fluid storage material comprises:
    at least one wicking layer; and
    at least one absorbent member.

5. The inline storage pouch of claim 1, wherein the fluid storage material comprises an absorbent member.

6. The inline storage pouch of claim 1, wherein the fluid storage material comprises an absorbent member, a first wicking member, and a second wicking member, wherein the absorbent member is at least partially disposed between the first wicking member and the second wicking member, and wherein the first wicking member and second wicking member are in fluid communication.

7. The inline storage pouch of claim 6, further comprising a plurality of fluid-communication buttons, wherein each fluid-communication button comprises an aperture formed in the fluid storage material and an attachment coupling the first wicking member and the second wicking member in the aperture.

8. The inline storage pouch of claim 1 wherein the flexible pouch body comprises:
   a first wall; and
   a second wall, wherein at least a portion of the wall and the second wall comprises a high-moisture-vapor-rate material.

9. The inline storage pouch of claim 1, further comprising:
   a first reduced-pressure indicator fluidly coupled to the interior portion of the flexible pouch body proximate the first port, wherein the first reduced-pressure indicator is for providing a visual indication of whether or not the first reduced-pressure indicator is experiencing a reduced pressure greater than a first threshold; and
   a second reduced-pressure indicator fluidly coupled to the interior portion of the flexible pouch body proximate the second port, wherein the second reduced-pressure indicator is for providing a visual indication of whether or not the second reduced-pressure indicator is experiencing a reduced pressure greater than a second threshold.

10. The inline storage pouch of claim 1, further comprising:
    a second bypass conduit disposed within and fluidly isolated from the interior portion of the flexible pouch body, the second bypass conduit having a first end and a second end;
    wherein the first end of the second bypass conduit is fluidly coupled to the interior portion of the flexible pouch body proximate the first port; and
    wherein the second multi-lumen conduit further comprises a first pouch-pressure-sensing conduit, and wherein the second end of the second bypass conduit is fluidly coupled to the first pouch-pressure-sensing conduit.

11. The inline storage pouch of claim 1, further comprising:
    a pouch-pressure-sensing pad fluidly coupled to the interior portion of the flexible pouch body proximate to the second port; and
    wherein the second multi-lumen conduit further comprises a first pouch-pressure-sensing conduit, and wherein the first pouch-pressure-sensing conduit is fluidly coupled to the pouch-pressure-sensing pad.

12. The inline storage pouch of claim 1, wherein the flexible pouch body has a first side and a second, animal-facing side, and wherein the first port is coupled to the flexible pouch body on the second, animal-facing side and the second port is coupled to the flexible pouch body on the first side.

13. An inline storage pouch for use with body fluids from an animal, the inline storage pouch comprising:
    a flexible pouch body having an interior portion;
    a fluid storage material disposed within the interior portion;
    a first port formed on the flexible pouch body configured to connect to a first multi-lumen conduit extending from the flexible pouch body to the animal, the first multi-lumen conduit having at least one sensing lumen and at least one reduced pressure lumen;
    a second port formed on the flexible pouch body configured to fluidly connect to a second multi-lumen conduit extending from the flexible pouch body to a reduced pressure source, the second multi-lumen conduit having at least one sensing lumen and at least one reduced pressure lumen; and
    a first bypass conduit disposed within and fluidly isolated from the interior portion of the flexible pouch body, the first bypass conduit having a first end and a second end, the first end of the first bypass conduit fluidly coupled to the at least one sensing lumen of the first multi-lumen conduit and the second end of the first bypass conduit fluidly coupled to the at least one sensing lumen of the second multi-lumen conduit; and
    a plurality of offsets disposed between the flexible pouch body and the fluid storage material.

14. A system for treating a tissue site on an animal with reduced pressure, the system comprising:
    a wound dressing for disposing proximate to the tissue site for providing reduced pressure to the tissue site, the wound dressing having a reduced-pressure interface, the reduced-pressure interface having a reduced-pressure-supply conduit and a pressure-assessment conduit;
    an inline storage pouch;
    a first multi-lumen conduit having at least one sensing lumen and at least one reduced pressure lumen, wherein the at least one sensing lumen is fluidly coupled to the pressure-assessment conduit of the reduced-pressure interface and the at least one reduced-pressure lumen is fluidly coupled to the reduced-pressure-supply conduit;
    wherein the inline storage pouch comprises:
      a flexible pouch body having an interior portion,
      a fluid storage material disposed within the interior portion,
      a first port formed on the flexible pouch body configured to connect to the first multi-lumen conduit,
      a second port formed on the flexible pouch body configured to fluidly connect to a second multi-lumen conduit extending from the flexible pouch body to a reduced pressure source, the second multi-lumen conduit having at least one sensing lumen and at least one reduced pressure lumen, and
      a first bypass conduit disposed within and fluidly isolated from the interior portion of the flexible pouch body, the bypass conduit having a first end and a second end, the first end fluidly coupled to the at least one sensing lumen of the first multi-lumen conduit and the second end fluidly coupled to the at least one sensing lumen of the second multi-lumen conduit;
    a reduced-pressure source;
    a first pressure-sensing unit;
    wherein the at least one reduced pressure lumen of the second multi-lumen conduit is fluidly coupled to the reduced-pressure source; and
    wherein the at least one sensing lumen of the second multi-lumen conduit is fluidly coupled to the first-pressure sensing device;
    wherein the first port comprises a patient-port interface coupled to the flexible pouch body, the patient-port interface comprising:
      a patient-port body having a first side and a second, pouch-facing side; and
      a first plurality of offsets formed on the second, pouch-facing side of the patient-port body for providing flow space.

15. The system of claim 14, further comprising:
    a second bypass conduit disposed within and fluidly isolated from the interior portion of the flexible pouch body, the second bypass conduit having a first end and a second end;
    wherein the first end of the second bypass conduit is fluidly coupled to the interior portion of the flexible pouch body proximate the first port; and wherein the second multi-lumen conduit further comprises a first pouch-pressure-sensing conduit, and wherein the second end of the second bypass conduit is fluidly coupled to the first pouch-pressure-sensing conduit;
a pouch-pressure-sensing pad fluidly coupled to the interior portion of the flexible pouch body proximate to the second port; and
wherein the second multi-lumen conduit further comprises a second pouch-pressure-sensing conduit, and wherein the second pouch-pressure-sensing conduit is fluidly coupled to the pouch-pressure-sensing pad.

16. The system of claim 15, further comprising:
a microprocessor;
a reduced-pressure source fluidly coupled to the at least one reduced pressure lumen of the second multi-lumen conduit;
a second pressure sensing unit fluidly coupled to the first pouch-pressure-sensing conduit of the second multi-lumen conduit;
a third pressure sensing unit fluidly coupled to the second pouch-pressure conduit of the second multi-lumen conduit; and
wherein the microprocessor is operatively coupled to the reduced-pressure source, the first pressure sensing unit, second pressure sensing unit, and third pressure sensing unit; and
wherein the microprocessor, reduced-pressure source, the first pressure sensing unit, second pressure sensing unit, and third pressure sensing unit are configured to:
determine a wound-site pressure,
compare the wound-site pressure to a selected pressure,
activate the reduced-pressure source if the wound-site pressure is less than the selected pressure,
determine the pressure at the second port, and
give an error flag indicating that a blockage exists between the reduced-pressure source and inline storage pouch if the reduced pressure at the second port is less than a first threshold pressure.

17. The system of claim 15, further comprising:
a microprocessor;
a reduced-pressure source fluidly coupled to the at least one reduced pressure lumen of the second multi-lumen conduit;
a second pressure sensing unit fluidly coupled to the first pouch-pressure-sensing conduit of the second multi-lumen conduit;
a third pressure sensing unit fluidly coupled to the second pouch-pressure conduit of the second multi-lumen conduit; and
wherein the microprocessor is operatively coupled to the reduced-pressure source, the first pressure sensing unit, second pressure sensing unit, and third pressure sensing unit; and
wherein the microprocessor, reduced-pressure source, the first pressure sensing unit, second pressure sensing unit, and third pressure sensing unit are configured to:
determine a wound-site pressure,
compare the wound-site pressure to a selected pressure,
activate the reduced-pressure source if the wound-site pressure is less than the selected pressure,
determine the pressure at the first port,
give an error flag indicating that the inline storage pouch is full if the reduced pressure at the first port is less than a second threshold and the reduced pressure at the second port is less than a first threshold pressure.

18. The system of claim 14, wherein the patient-port interface further comprising:
wherein the patient-port body comprises a first hollow attachment connector for mating with the at least one reduced pressure lumen;
a first fluid outlet formed on the patient-port body and fluidly coupled to the first hollow attachment connector;
wherein the patient-port body comprises a second hollow attachment connector for mating with the at least one sensing lumen;
a first pressure-sensing connector fluidly coupled to the second hollow attachment connector, the pressure-sensing connector for coupling to the first bypass conduit.

19. The system of claim 14, wherein the second port comprises a device-port interface, the device-port interface comprising:
a device-port body having a first side and a second, pouch-facing side;
wherein the device-port body comprises a third hollow attachment connector for mating with the at least one reduced pressure lumen;
a fluid inlet formed on the device-port body and fluidly coupled to the third hollow attachment connector;
wherein the device-port body comprises a fourth hollow attachment connector for mating with the at least one sensing lumen;
a second pressure-sensing connector fluidly coupled to the fourth hollow attachment connector, the second pressure-sensing connector for coupling to the first bypass conduit; and
a second plurality of offsets formed on the second, pouch-facing side of the device port body for providing flow space.

20. The system of claim 14, wherein the fluid storage material comprises:
at least one wicking layer; and
at least one absorbent member.

21. The system of claim 14, wherein the fluid storage material comprises an absorbent member.

22. The system of claim 14, wherein the fluid storage material comprises an absorbent member, a first wicking member, and a second wicking member, wherein the absorbent member is at least partially disposed between the first wicking member and the second wicking member, and wherein the first wicking member and second wicking member are in fluid communication.

23. The system of claim 14, further comprising:
a first reduced-pressure indicator fluidly coupled to the interior portion of the flexible pouch body proximate the first port, wherein the first reduced-pressure indicator is for providing a visual indication of whether or not the first reduced-pressure indicator is experiencing a reduced pressure greater than a first threshold; and
a second reduced-pressure indicator fluidly coupled to the interior portion of the flexible pouch body proximate the second port, wherein the second reduced-pressure indicator is for providing a visual indication of whether or not the second reduced-pressure indicator is experiencing a reduced pressure greater than a second threshold.

24. The system of claim 22, further comprising a plurality of fluid-communication buttons, wherein each fluid-communication button comprises an aperture formed in the fluid storage material and an attachment coupling the first wicking member and the second wicking member in the aperture.

25. An inline storage pouch for use with body fluids from an animal, the inline storage pouch comprising:
- a flexible pouch body having an interior portion;
- a fluid storage material disposed within the interior portion;
- a first port formed on the flexible pouch body configured to connect to a first multi-lumen conduit extending from the flexible pouch body to the animal, the first multi-lumen conduit having at least one sensing lumen and at least one reduced pressure lumen;
- a second port formed on the flexible pouch body configured to fluidly connect to a second multi-lumen conduit extending from the flexible pouch body to a reduced pressure source, the second multi-lumen conduit having at least one sensing lumen and at least one reduced pressure lumen; and
- a first bypass conduit disposed within and fluidly isolated from the interior portion of the flexible pouch body, the first bypass conduit having a first end and a second end, the first end of the first bypass conduit fluidly coupled to the at least one sensing lumen of the first multi-lumen conduit and the second end of the first bypass conduit fluidly coupled to the at least one sensing lumen of the second multi-lumen conduit;
- wherein the first port comprises a patient-port interface coupled to the flexible pouch body, the patient-port interface comprising a patient-port body having a first plurality of offsets formed on a second, pouch-facing side of the patient-port body for providing flow space.

26. A system for treating a tissue site on an animal with reduced pressure, the system comprising:
- a wound dressing for disposing proximate to the tissue site for providing reduced pressure to the tissue site, the wound dressing having a reduced-pressure interface, the reduced-pressure interface having a reduced-pressure-supply conduit and a pressure-assessment conduit;
- an inline storage pouch;
- a first multi-lumen conduit having at least one sensing lumen and at least one reduced pressure lumen, wherein the at least one sensing lumen is fluidly coupled to the pressure-assessment conduit of the reduced-pressure interface and the at least one reduced-pressure lumen is fluidly coupled to the reduced-pressure-supply conduit;
- wherein the inline storage pouch comprises:
  - a flexible pouch body having an interior portion,
  - a fluid storage material disposed within the interior portion,
  - a first port formed on the flexible pouch body configured to connect to the first multi-lumen conduit,
  - a second port comprising a device-port body having a first side, and a second, pouch-facing side, the second port formed on the flexible pouch body configured to fluidly connect to a second multi-lumen conduit extending from the flexible pouch body to a reduced pressure source, the second multi-lumen conduit having at least one sensing lumen and at least one reduced pressure lumen,
  - a plurality of offsets formed on the second, pouch facing side of the device port body for providing flow space, and
  - a first bypass conduit disposed within and fluidly isolated from the interior portion of the flexible pouch body, the bypass conduit having a first end and a second end, the first end fluidly coupled to the at least one sensing lumen of the first multi-lumen conduit and the second end fluidly coupled to the at least one sensing lumen of the second multi-lumen conduit;
- a reduced-pressure source;
- a first pressure-sensing unit;
- wherein the at least one reduced pressure lumen of the second multi-lumen conduit is fluidly coupled to the reduced-pressure source; and
- wherein the at least one sensing lumen of the second multi-lumen conduit is fluidly coupled to the first-pressure sensing device.

* * * * *